US012709774B2

(12) United States Patent
Guo et al.

(10) Patent No.: US 12,709,774 B2
(45) Date of Patent: Aug. 18, 2026

(54) ULTRA-HIGH-THROUGHPUT SINGLE CELL SEQUENCING METHOD

(71) Applicant: ZHEJIANG UNIVERSITY, Zhejiang (CN)

(72) Inventors: Guoji Guo, Hangzhou (CN); Yuan Liao, Hangzhou (CN); Haide Chen, Hangzhou (CN); Xiaoping Han, Hangzhou (CN); Jingjing Wang, Hangzhou (CN); Guodong Zhang, Hangzhou (CN); Lei Yang, Hangzhou (CN)

(73) Assignee: ZHEJIANG UNIVERSITY, Hangzhou (CN)

( * ) Notice: Subject to any disclaimer, the term of this patent is extended or adjusted under 35 U.S.C. 154(b) by 1102 days.

(21) Appl. No.: 17/785,045

(22) PCT Filed: Sep. 17, 2021

(86) PCT No.: PCT/CN2021/119166

§ 371 (c)(1),
(2) Date: Jun. 13, 2022

(87) PCT Pub. No.: WO2022/237035

PCT Pub. Date: Nov. 17, 2022

(65) Prior Publication Data

US 2024/0182962 A1 Jun. 6, 2024

(30) Foreign Application Priority Data

May 12, 2021 (CN) ......................... 202110517750.6
Aug. 9, 2021 (CN) ......................... 202110911428.1

(51) Int. Cl.

| | |
|---|---|
| ***C12Q 1/6869*** | (2018.01) |
| ***C12N 15/10*** | (2006.01) |
| ***C12Q 1/25*** | (2006.01) |
| ***C12Q 1/6806*** | (2018.01) |
| ***C12Q 1/686*** | (2018.01) |

(52) U.S. Cl.

CPC ....... *C12Q 1/6869* (2013.01); *C12N 15/1072* (2013.01); *C12Q 1/25* (2013.01); *C12Q 1/6806* (2013.01); *C12Q 1/686* (2013.01); *G01N 2333/9015* (2013.01)

(58) Field of Classification Search

None

See application file for complete search history.

(56) References Cited

U.S. PATENT DOCUMENTS

2018/0346970 A1* 12/2018 Chang .................. C12Q 1/6811
2020/0056231 A1* 2/2020 Lebofsky .............. G16B 40/10

FOREIGN PATENT DOCUMENTS

CN 106498040 3/2017
CN 110684829 1/2020
CN 111088250 5/2020

OTHER PUBLICATIONS

Datlinger et al., "Ultra-high throughput single-cell RNA sequencing by combinatorial fluidic index". BioRxiv, Dec. 18, 2019, pp. 1-27.

* cited by examiner

*Primary Examiner* — Heather Calamita
*Assistant Examiner* — Jessica D Parisi
(74) *Attorney, Agent, or Firm* — Jiwen Chen; Joywin IP Law PLLC

(57) ABSTRACT

The present invention discloses an ultra-high-throughput single cell sequencing method, the method of the present invention including: firstly performing intracellular reverse transcription by using a reverse transcription sequence, or firstly performing intranuclear transposition of a transposase-accessible chromatin genome sequence by using a specific molecular barcode transposase-embedded complex, then compartmentalizing one or more cells or nuclei with one molecular labeled microbead by microwell-plate technology or microfluidic technology, followed by lysis of the cells or nuclei under the action of a lysis buffer, ligation of the sequences with the molecular label sequence on the molecular labeled microbeads through bridge primers, and PCR amplification to obtain a large quantity of sequences for construction of cDNA sequencing library, and then performing high-throughput sequencing, where information of specific transcriptome/genome accessibility of millions of single cells can be obtained in one run of sequencing. The throughput of single cell sequencing is highly improved.

12 Claims, 9 Drawing Sheets

Specification includes a Sequence Listing.

ULTRA-HIGH-THROUGHPUT SINGLE CELL SEQUENCING METHOD

This is a U.S. national stage application of PCT Application No. PCT/CN2021/119166 under 35 U.S.C. 371, filed Sep. 17, 2021 in Chinese, claiming priority to Chinese Patent Application No. 202110517750.6, filed May 12, 2021 and Chinese Patent Application No. 202110911428.1, filed Aug. 9, 2021, all of which are hereby incorporated by reference. The amended Sequence Listing in ASCII text file (CRF format) with the file name of P76308US0_SEQ_LIST_ST25.txt, created on June 2022 and with the size of 3992 bytes is also incorporated by reference. It is respectfully submitted that the Sequence Listing in CRF format does not include new matter. In addition, the Sequence Listings hereby submitted satisfy both the paper copy requirement under 37 CFR 1.821 (c) and the computer-readable form requirement of 37 CFR 1.182 (e). Thus, the requirement of 37 CFR 1.821 (f) has been satisfied.

FIELD OF TECHNOLOGY

The present invention relates to the technical field of single cell sequencing, particularly to an ultra-high-throughput single cell sequencing method.

BACKGROUND TECHNOLOGY

Since the introduction of single cell sequencing technology by Fuchou Tang in 2009, single cell high-throughput sequencing platforms have sprung up, such as microfluidics-based Drop-seq and inDrop-seq platforms, microwell plate-based Microwell-seq and Seq-well platforms as well as the common commercial platform 10×Genomics. However, taking microwell plate as an example, when cell input is up to a certain level, it is easy to have two or even more cells captured in one microwell, resulting in contamination of transcripts between cells. To avoid this phenomenon, it was found by analysis that each bead capturing only one cell can be achieved when the capture rate of cells in the microwell plate is approximately 1/10 of the total number of wells in the microwell plate. However, this will result in a large number of droplets or microwells having empty microbeads only but without cells in them, which greatly reduces experimental efficiency while increasing the cost, leading to cell throughput per run on these platforms in the order of magnitude of tens of thousands only. However, the total number of cells in a single individual of a species, taking mice and humans as examples, exceeds trillions. Therefore, the current platform throughput is far from meeting sequencing requirements. Insufficient sequencing throughput tends to result in loss of a large amount of biological information, so it is especially important to improve the throughput per sequencing run.

Recent years have seen a continuous development of ultra-high-throughput technologies using individual cells as independent reaction systems, such as sci-RNA-seq and SPLiT-seq, these technologies including: firstly fixing and permeabilizing fresh cells and incorporating a round of unique molecular label into each cell by reverse transcription, followed by incorporating different molecular labels to the cells through split-pool, such that the transcript in each cell is finally incorporated with a unique molecular label through multiple combinations of molecular labels, thus greatly improving the throughput per run. However, since these methods are based on intracellular ligation reactions, there are problems such as low reaction efficiency and high contamination rate because of easy leakage of transcripts between cells, which reduce the practicality of the methods.

Paul et al. (Datlinger, P., et al., Ultra-high throughput single-cell RNA sequencing by combinatorial fluidic indexing. BioRxiv, 2019.) from CeMM Research Center for Molecular Medicine of the Austrian Academy of Sciences increased the throughput of single-cell sequencing up to 15-fold in December 2019 by a method of introducing a round of 96/384 types of molecular labels to fixed cells with reverse transcription followed by combinatorial microfluidics. However, cells are not sequenced in a parallel way on microfluidics-based sequencing platforms, leading to more significant batch effect with abnormal UMI/Gene ratios, and moreover, there are disadvantages including expensive equipment, difficulty to carry, and high sequencing cost.

In a genome, most of the chromatin is tightly wound in the nucleus and is transcriptionally inactive. Chromatin state is dynamically regulated in a cell type-specific manner, with some of the dense chromatin becoming loose in a specific cell state, these loose chromatins being referred to as open chromatin or accessible chromatin. Assay for chromatin accessibility in cells can give information on transcription regulation in cells, such as where transcription factors can bind to gene promoters and which genes of the cells may be efficiently transcribed. The commonly used assays are ATAC-seq, DNase-seq, MNase-seq, FAIRE-seq, ChIP-seq, etc. These methods include fragmenting and tagmenting open chromatin regions based on different principles, among which ATAC-seq (assay for transposase-accessible chromatin with high-throughput sequencing) employs a modified Tn5 transposase that randomly inserts a specific DNA sequence as a transposon into an open chromatin region, and can capture the entire open-region sequence directly in an intact manner, so ATAC-seq is currently widely used in open chromosome sequencing.

SUMMARY OF THE INVENTION

The present invention provides an ultra-high-throughput single cell sequencing method, which can obtain specific transcriptome information of millions of single cells per run.

First, the present invention provides an ultra-high-throughput single cell sequencing method, comprising the following steps:

(1) preparing the following reagents:

a) molecular labeled microbeads, the molecular labeled microbead comprising a microbead body and a coupled molecular label sequence, the molecular label sequence comprising in sequence:

a universal primer sequence, serving as a primer binding region during PCR amplification;

a first cell barcode sequence; and a first bridge sequence;

b) a reverse transcription sequence for intracellular reverse transcription, the reverse transcription sequence comprising in sequence:

a second bridge sequence;

a second cell barcode sequence, forming a cell barcode sequence in conjunction with the first cell barcode sequence, the cell barcode sequence being used for identifying a cell from which an mRNA to which each sequence in a constructed sequencing library corresponds is derived;

a molecular barcode sequence for identifying mRNA to which each sequence in a constructed sequencing library corresponds;

a poly-T tail for complementary pairing with intracellular mRNA with a poly-A sequence; and c) a bridge primer for ligating the above-mentioned label sequence in a) and the reverse transcription sequence in b), the bridge primer having, on both ends, a sequence complementary to the first bridge sequence and the second bridge sequence, respectively;

(2) adding the reverse transcription sequence to a cell sample to be sequenced for intracellular reverse transcription such that the poly-T tail of the reverse transcription sequence is ligated with a cDNA sequence derived from reverse transcription of the intracellular mRNA sequence to obtain a reverse transcription sequence-cDNA sequence;

(3) compartmentalizing one or more of the intracellularly reverse-transcribed cells from step (2) with one molecular labeled microbead by microwell-plate technology or microfluidic technology, and lysing the cells under the action of a lysis buffer, incubating, and then ligating the first bridge sequence with the second bridge sequence by the pairing of bridge primers with the first bridge sequence and the second bridge sequence, respectively, followed by ligation through a ligase, such that a molecular label sequence—reverse transcription sequence—cDNA sequence coupled to the microbead is obtained;

(4) collecting the microbeads coupled with the molecular label sequence—reverse transcription sequence—cDNA sequence, and performing PCR amplification to obtain a cDNA sequence having the first cell barcode sequence, the second cell barcode sequence and the molecular barcode sequence; and (5) constructing a cDNA sequencing library with the product obtained from step (4), and then performing high-throughput sequencing to obtain information of specific transcriptome of millions of single cells.

The sequencing method is a transcriptome sequencing method. By dividing the cell barcode sequence into a first cell barcode sequence and a second cell barcode sequence, and by introducing the second cell barcode sequence in the form of a reverse transcription sequence int o the reverse transcription sequence of each mRNA during intracellular reverse transcription, a plurality of cells can be distinguished based on the second cell barcode sequence, in the event that a molecular labeled microbead binds to a plurality of cells; otherwise, it would be impossible to distinguish sequences derived from a plurality of cells that bind to the same molecular labeled microbead by relying solely on the first cell barcode sequence on the molecular labeled microbead. In the prior art, in order to avoid one molecular labeled microbead binding to a plurality of cells, strict condition control is required, for example, the microwells on the microwell plate for the experiment should be prepared as well as possible, such that the size of the microwells is for accommodating only one molecular labeled microbead and one cell (In this case, the relative size of the molecular labeled microbeads and the cells should not be too large; otherwise, it will be difficult to achieve one molecular labeled microbead binding to one cell); and meanwhile, it is also necessary to control the cell capture rate at a relatively low level so that the cells are well dispersed. However, it is still impossible to avoid one molecular labeled microbead binding to a plurality of cells, in which case the sequences will be wrongly determined as originating from a same cell according to the final sequencing result.

Meanwhile, the combination of the second cell barcode sequence and the first cell barcode sequence to form a cell barcode sequence increases the number of combinations of cell barcode sequences, thus enabling assay for cells of larger quantities in one run.

The present invention further provides an ultra-high-throughput single cell sequencing method, comprising the following steps:

(1) preparing the following reagents:

a) molecular labeled microbeads, the molecular labeled microbead comprising a microbead body and a coupled molecular label sequence, the molecular label sequence comprising in sequence:

a universal primer sequence, serving as a primer binding region during PCR amplification;

a first cell barcode sequence; and a first bridge sequence;

b) a specific molecular barcode transposase-embedded complex, comprising Tn5 transposase and a specific molecular barcode sequence, wherein the specific molecular barcode sequence comprises in sequence:

a second bridge sequence;

a second cell barcode sequence, forming a cell barcode sequence in conjunction with the first cell barcode sequence, the cell barcode sequence being used for identifying a cell from which each sequence in the constructed sequencing library is derived; and a Mosaic Ends sequence for binding to the Tn5 transposase, the Mosaic Ends sequence having a double-stranded structure, wherein one strand is ligated with the second cell barcode sequence; and c) a bridge primer for ligating the above-mentioned label sequence in a) and the specific molecular barcode sequence in b), the bridge primer having, on both ends, a sequence complementary to the first bridge sequence and the second bridge sequence, respectively;

(2) extracting nuclei from a cell sample to be sequenced;

(3) adding the specific molecular barcode transposase-embedded complex to the extracted nuclei of the step (2) for transposition reaction;

(4) compartmentalizing one or more of the transposed nuclei with one molecular labeled microbead by microwell-plate technology or microfluidic technology, and lysing the nuclei under the action of a lysis buffer, incubating, and then ligating the first bridge sequence with the second bridge sequence by pairing of the bridge primers with the first bridge sequence and the second bridge sequence, respectively, followed by ligation through a ligase, such that a molecular label sequence—specific molecular barcode sequence—transposase-accessible chromatin genome sequence coupled to the microbead is obtained;

(5) collecting the microbeads coupled with the molecular label sequence—specific molecular barcode sequence—transposase-accessible chromatin genome sequence, and performing PCR amplification to obtain a transposase-accessible chromatin genome sequence having the first cell barcode sequence, the second cell barcode sequence and the specific molecular barcode sequence; and (6) constructing a chromatin accessibility sequencing library with product obtained from step (5), and then performing high-throughput sequencing to obtain information of transposase-accessible chromatin genome sequence of millions of single cells.

The sequencing method is an assay for transposase-accessible chromatin sequencing method. By dividing the cell barcode sequence into a first cell barcode sequence and a second cell barcode sequence, and by incorporating the second cell barcode sequence into the corresponding sequence of a genome during transposition reaction with Tn5 transposase, a plurality of cells can be distinguished based on the second cell barcode sequence in the event that a molecular labeled microbead binds to a plurality of cells; otherwise, it would be impossible to distinguish sequences derived from a plurality of cells that bind to the same molecular labeled microbead by relying solely on the first cell barcode sequence on the molecular labeled microbead.

Preferably, the microbead is coupled to the molecular label sequence in such a way comprising: replacing the hydroxyl group with an amine group at the C6 position of the nucleotide at the 5' end of the molecular label sequence, having a surface of the microbead modified with a carboxyl group, and coupling through condensation of the amino group and the carboxyl group. Since the molecular label sequence is a single-stranded oligonucleotide, the hydroxyl group on the first nucleotide at its 5' end being replaced with an amine group, and the surface of the microbead is modified with a carboxyl group, the molecular label sequence is coupled to the microbead through the reaction of the amino group and the carboxyl group.

Preferably, at least a part of the molecular label sequence is a random sequence that is randomly synthesized.

Preferably, the first cell barcode sequence comprises a plurality of specific fragments, and the second cell barcode sequence comprises at least one specific fragment, the specific fragments at different locations being selected from the same or different libraries of specific fragments, and the first cell barcode sequence and the second cell barcode sequence identifying cells by using different combinations and arrangements of the specific fragments.

Further preferably, the preparation method of the molecular labeled microbead comprises the following step:

(1) classifying the primers for synthesizing the molecular label sequences into a plurality of primers in accordance with the number of the specific fragments, each primer comprising a specific fragment, there being adapter sequences between each of the primers for bridging, ligation and complementing each other, wherein the primer corresponding to the 5' end of the molecular label sequence further comprises the universal primer sequence, and the primer corresponding to the 3' end of the molecular label sequence further comprises the first bridge sequence; and (2) coupling the primer corresponding to the 5' end of the molecular label sequence to the microbead body, then annealing and extending the remaining primers in sequence by PCR, and cascading the remaining specific fragments of the molecular label sequence in sequence from the 5' end to the 3' end to prepare and obtain the molecular labeled microbead.

Preferably, the molecular label sequence is: 5'-TTTAGGGATAACAGGGTAATAAGCAGTGGTATCAACGCAGAGTACGTNNNNNNNCG ACTCACTACAGGGNNNNNNTCGGTGACACGATCGNNNN NNTCGTCGGCAGCGTC-3' (SEQ ID No. 4), wherein, N represents any one of A/T/C/G and is randomly synthesized. The reverse transcription sequence is: 5'-[phos]ACACTCTTTCCCTACACGACGNNNNNNnnnnnnnnnn TTTTTTTTTTTTTTTTTTT TTTTTTVN-3'(SEQ ID No. 6), wherein, the phosphorylation modification at the 5' end provides a phosphate group for the ligation reaction; N represents any one of A/T/C/G and is randomly synthesized; n represents any one of A/T/C/G and is randomly synthesized; and V at the 3' end represents any one of A/C/G with V being randomly synthesized. The specific molecular barcode sequence is: 5'-ACACTCTTTCCCTACACGACGNNNNNNNNNNAGATGTGTATAAGAGACAG-3'(SEQ ID No. 11), wherein, N represents any one of A/T/C/G and is randomly synthesized; the complementary Mosaic Ends sequence to form a double strand is: 5'-CTGTCTCTTATACACATCT-3' (SEQ ID No. 12). The bridge primer is: 5'-CGTCGTGTAGGGAAAGAGTGTGACGCTGCCGACGA[ddC]-3'(SEQ ID No. 5), wherein ddC is dideoxycytidine modification. Alternatively, the ddC at the 3' end can be removed. In the reverse transcription sequence, the 6×N random sequence is used as the second cell barcode sequence, and the 10×n random sequence is used as the molecular barcode sequence.

For ATAC-seq (assay for transposase-accessible chromatin with high-throughput sequencing), one transposase complex of the specific molecular barcode transposase-embedded complex carries two gene fragments, both gene fragments being the specific molecular barcode sequence; alternatively, one gene fragment being the specific molecular barcode sequence and the other gene fragment being a universal sequence, the universal sequence comprising:

a primer binding sequence for amplification, serving as a primer binding region during PCR amplification;

a Mosaic Ends sequence for binding to the Tn5 transposase, the Mosaic Ends sequence having a double-stranded structure, wherein one strand is ligated with the primer binding sequence for amplification.

Preferably, the cell sample to be sequenced comprises 2 or more types of cells. The ultra-high-throughput single cell sequencing method of the present application can realize parallel sequencing of multiple types of cells.

Preferably, the microbead body is a magnetic bead; intracellularly reverse transcribed cells (reverse transcription sequencing) or transposed nuclei (ATAC-seq) are added to a microwell plate, followed by the addition of the molecular labeled microbead, the microwell in the microwell plate having a diameter big enough to just accommodate one molecular labeled microbead and one or more cells or nuclei; the capture rate of cells or nuclei in the microwell plate is maintained at over 80%; and the capture rate of the molecular labeled microbead in the microwell plate is over 99%.

The ultra-high-throughput single cell sequencing method of the present application can achieve one molecular labeled microbead binding a plurality of cells, therefore, in the case of the microbead body being a magnetic bead and in the case of using the microwell plate method, the capture rate of cells in microwell plates can be greatly improved.

Besides of being used for microwell plate-based single cell sequencing with the microbead body being a magnetic bead, the present invention may also be used for microfluidics-based single cell sequencing platforms.

Further preferably, the microwell depth in the microwell plate is 30-160 μm and the microwell diameter is 20-150 μm; and the diameter of the microbead body is 20-145 μm.

Further preferably, the preparation method of the microwell plate is: (1) etching microwells on a silicon wafer as an initial mold; (2) pouring polydimethylsiloxane over the initial mold and removing the polydimethylsiloxane after molding to produce a second mold with microwells; and (3) pouring molten agarose with a mass to volume ratio of 4% to 6% on the second mold, cooling and molding followed by removing the agarose to obtain the microwell plate.

The ultra-high-throughput single cell sequencing method of the present invention can be used for ultra-high-throughput sequencing of millions of single cells, with the number of cells per run up to millions of single cells, thereby greatly improving the throughput of single cell sequencing.

DETAILED DESCRIPTION OF THE EMBODIMENTS

Embodiment 1

1. Preparation of Microwell Plates

Figure 1:
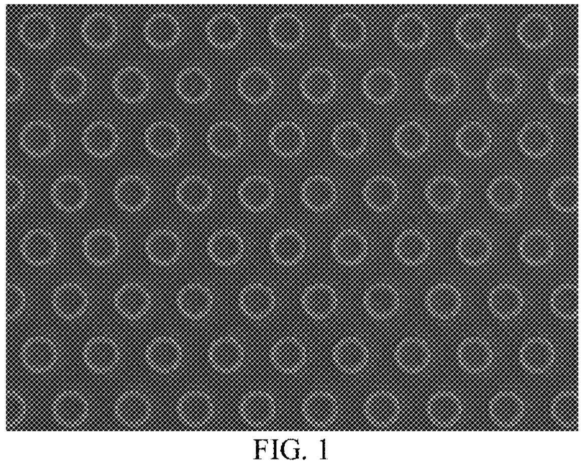
FIG. 1 is a schematic diagram of a hexagonally-packed microwell plate.

The size of a microwell plate was designed according to the experimental scale (e.g., in the case of 500,000 each of human 293T cells and mouse 3T3 cells, the well plate size was 1.8 cm×1.8 cm), and microwells were etched on a silicon wafer as the initial mold, the microwells being cylindrical, wherein the microwell depth was 60 μm, the microwell diameter was 50 μm, and the well spacing was 70 μm. Next, polydimethylsiloxane (PDMS) was poured on the silicon wafer, and the PDMS was removed after molding to produce a second mold with micropillars on the plate. The finished microwell plate used in the experiment was prepared by pouring molten agarose (prepared with enzyme-free water) with a concentration of 5% (mass ratio) into the PDMS micropillar plate, cooling and solidifying, the agarose-plate casting being peeled off to produce a microwell plate of a certain thickness (FIG. 1). The microwell plates can be stored in a cell-friendly DPBS-EDTA mix in a 4° C. refrigerator with lid on, while preparation before use will ensure a good working condition of the microwell plate.

2. Preparation of Molecular Labeled Magnetic Beads

Figure 2:
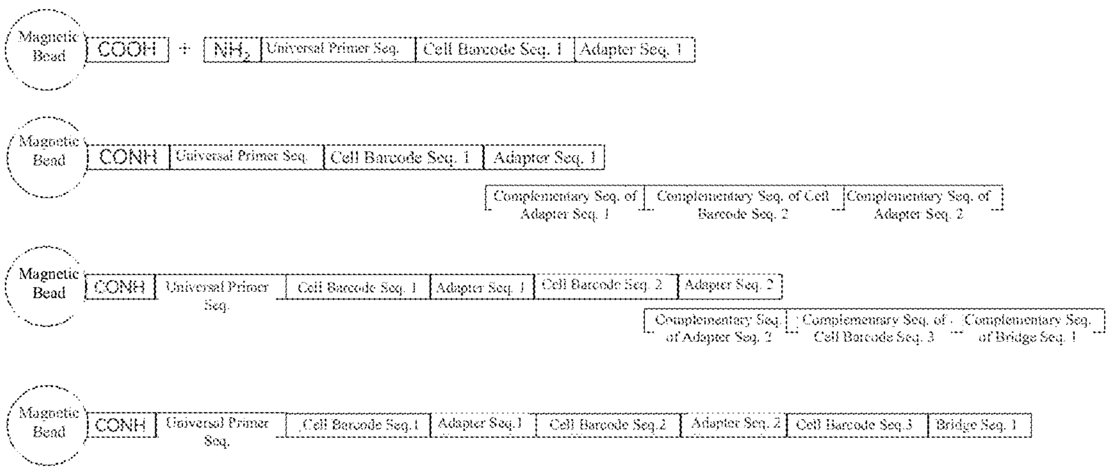
FIG. 2 is a flow chart of the preparation of molecular labeled magnetic beads.

The magnetic beads were purchased from Suzhou Knowledge & Benefit Sphere Tech. Co., Ltd (cat #MagCOOH-20190725), which are coated with carboxyl groups on the surface and have a diameter of 45 μm. The preparation process of the molecular labeled magnetic beads is as shown in FIG. 2, comprising the following four (4) steps:

(1) The molecular label sequence was designed in such a way that it was divided into three segments, with an adapter sequence arranged between two adjacent segments for connecting the two adjacent segments by PCR, wherein the first segment starting with a 5' end comprised a universal primer sequence and a part of a cell barcode sequence, and the last segment comprised a part of the cell barcode sequence and the whole molecular barcode sequence and the complementary bridge sequence, and all the sequences except for the first segment were complementary sequences of the corresponding sequences.

(2) See Table 1 for each sequence segment.

TABLE 1

| | |
|---|---|
| First segment | 5'-TTTAGGGATAACAGGGTAATAAGCAGTGGTATCAACGCAGAGTACGTNNNNNNCGACTCACTACAGGG-3' (SEQ ID No. 1) |
| Second segment | 5'-CGATCGTGTCACCGANNNNNNCCCTGTAGTGAGTCG-3' (SEQ ID No. 2) |
| Third segment | 5'-GACGCTGCCGACGANNNNNNCGATCGTGTCACCGA-3' (SEQ ID No. 3) |

Wherein, 6×N was the core sequence of the cell barcode sequence, this core sequence corresponding to each magnetic bead being different, and the 6×N sequences in the three sequence segments corresponding to a same magnetic bead being different as well. Since there are four options from A/T/C/G for each site, there were $4^6$ options for the 6×N sequence. N represents any one of A/T/C/G and was randomly synthesized.

(3) All sequences were synthesized separately, wherein 96 types of sequences were designed for all the parts that belonged to the cell barcode sequence among all sequences, each of the 96 types of sequences being arranged independently, and the hydroxyl group at the C6 position of the nucleotide at the 5' end of the first sequence segment was replaced by an amine group.

(4) Equal amount of magnetic beads were coupled with 96 types of the first sequence segment separately and then collected to obtain 96 types of modified magnetic beads, which were mixed evenly and then divided into 96 aliquot parts and mixed with 96 types of the second sequence segment for sequence extension with PCR, followed by being divided into 96 aliquot parts again and mixed with 96 types of the third sequence segment for sequence extension with PCR, followed by denaturation and unwinding to obtain magnetic beads with 96×96×96 types of single-stranded oligonucleotide modifications.

Once completed, the molecular label sequence was as follows: 5'-TTTAGGGATAAC AGGGTAATAAGCAGTGGTAT-CAACGCAGAGTACGTNNNNNNCGACTCACTA-CAGGGN NNNNNTCGGTGACAC-GATCGNNNNNNTCGTCGGCAGCGTC-3'(SEQ ID No. 4), and could be used for ultra-high-throughput single cell sequencing.

Embodiment 2

Specific transcriptome ultra-high-throughput single cell sequencing.

1. Assay for Mixed Human 293T and Mouse 3T3 Cells

Mouse embryonic stem cells (ESC) 3T3 and human embryonic kidney cells (293T), 5 million each, were fixed at −20° C. for 30 min separately by slowly dripping 5-10 ml of methanol (pre-chilled at −20° C.) into the cells. Meanwhile, the bridge primers were dispensed into an 8-tube stripe, 6.5 μl per tube, and then dispensed into a 96-well plate containing 0.5 μl of the reverse transcription primer to mix well and stand still such that there were a total of 1 μl of mixed primers for reverse transcription per well. The sequence of the bridge primer was 5'-CGTCGTGTAGG-GAAAGAGTGTGACGCTGCCGACGA[ddC]-3'(SEQ ID No. 5), the ddC modification being added to the 3' end to prevent the production of byproducts resulted from extension of the bridge primer during reverse transcription.

There were 96 types of reverse transcription primers (reverse transcription sequences), the same as the above-mentioned cell barcode sequence, with the core sequence of 6×N, and each type of primer was arranged independently in each well. The 6×N random sequence could be used as a part of the cell barcode sequence, and subsequently used in conjunction with the cell barcode sequence on the molecular labeled magnetic beads in Embodiment 1 to identify the cells from which the mRNA corresponding to each sequence in the sequencing library constructed subsequently is derived, thus there being a total of 96×96×96×96 types of single-stranded oligonucleotides for identifying cells, sufficient to be used for millions of cells per run. Phosphorylation modification was added to the 5' end of the molecular barcode sequence of the last segment of the reverse transcription primer to provide phosphate groups for the ligation reaction, wherein n of 10×n represents any one of A/T/C/G and was randomly synthesized, V at the 3' end denotes any one of A/C/G, and N denotes any one of A/T/C/G and was randomly synthesized, with the main purpose of having the primer bind to the end of the polyA tail while avoiding the binding of the primer to the middle part of the polyA tail. The specific sequence of the reverse transcription primer was as follows: 5'-[phos]ACACTCTTTCCCTA-CACACGACGNNNNNNNnnnnnnnnnnnnnnnnn TTTTTTTTTTTTTTT TTTTTTTTTTTTVN-3'(SEQ ID No. 6).

Figure 3:
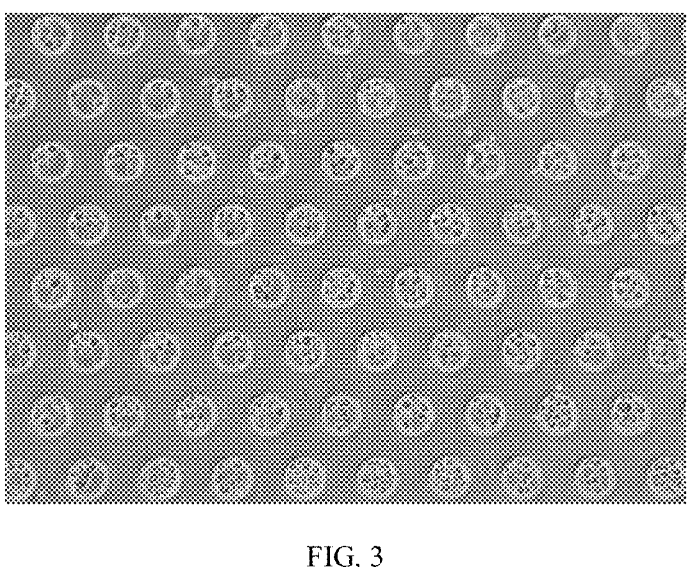
FIG. 3 is a schematic diagram of cells captured in a microwell plate.

310 μl of a reverse transcription system (50 μl of dNTP, 200 μl of buffer, 50 μl of reverse transcriptase and 10 μl of RNAase inhibitor) was prepared, mixed well, and dispensed into a 96-well plate containing mixed primers for reverse transcription, 3.1 μl per well. Next the two types of fixed cells were washed once by centrifugation at 500 g, and 2.5 million cells each were mixed. The mixed cells (approximately 50,000 cells per well) were dispensed evenly into a 96-well plate containing a pre-mixed reverse transcription system (6 μl of cell suspension, 0.5 μl of dNTP, 1 μl of mixed primers for reverse transcription, 2 μl of buffer, 0.5 μl of reverse transcriptase and 0.1 μl of RNAase inhibitor) to react at 42° C. for 1.5 hours. After reverse transcription, the cells in the 96-well plate were first collected into an 8-tube stripe using a multichannel pipette, then collectively transferred to a clean 1.5 ml EP tube, washed once with DPBS solution (Gibco, Cat #14190-144), and centrifuged at 500 g for 5 min. After aspiration of the supernatant, the cells were resuspended in 500 μl of DPBS solution, and then the cell suspension was dripped into a microwell plate such that greater than 80% of the microwells were occupied by cells (FIG. 3). 200,000 molecular labeled magnetic beads were loaded on the cell-occupied microwell plate which was placed on a magnet and mixed well gently so that the magnetic beads covered greater than 99% of the microwells. Excess molecular labeled magnetic beads were washed away with DPBS solution. 200 μl of a lysis solution ($ddH_2O$, 10% SDS, 50% formamide (vol/vol) and 3×SSC) was dripped slowly into the microwell plate covered by magnetic beads for lysis incubation at room temperature for 30 min to allow sufficient complementary hybridization of the bridge sequence on the magnetic beads and the bridge primers on the cells. After incubation, the microwell plate was inverted onto a magnet so that the magnetic beads with molecular label-mRNA complex were collected, transferred to an 1.5 ml EP tube and washed twice. The residual liquid was aspirated with a 20 μl pipette. 50 μl of ligation mix (2 μl of T4 ligase, 5 μl of T4 buffer, 1 μl of RNase inhibitor, 2 μl of dNTP, 5 μl of 30% PEG8000 and 35 μl of $ddH_2O$) was added to the EP tube containing the molecular labeled magnetic beads to react at 37° C. for 1 hour.

After completion of the ligation reaction, the molecular labeled magnetic beads were washed three times on a magnetic rack, the supernatant being aspirated and discarded, and 200 μl of exonuclease EXON I mix (EXON I buffer 1× and EXON I 1×) was added to react at 37° C. for 0.5 hour to remove from the magnetic beads the oligonucleotides which did not capture mRNA. After the exonucleolytic cleavage, the molecular labeled magnetic beads were washed three times on a magnetic rack, the supernatant being aspirated and discarded, and 500 μl of 0.1% NaOH solution was added for 5 min treatment to obtain single-stranded cDNA for the subsequent second strand synthesis reaction. The NaOH-treated molecular labeled magnetic beads were washed three times on a magnetic rack to remove residual NaOH, and then 100 μl of a second strand synthesis mix (20 μl of reverse transcription buffer, 40 μl of 30% PEG8000, 10 μl of 10 mM dNTP, 10 μl of 100 μM random primer, 2.5 μl of Klenow polymerase, and 17.5 μl of $ddH_2O$) was added to react at 37° C. for 1 hour, wherein the random primer sequence was 5'-AAGCAGTGGTAT-CAACGCAGAGTGANNNGGNNNB-3'(SEQ ID No. 7), where B represents one of G/T/C, and N represents any one of A/T/C/G and was randomly synthesized. The random primer sequence would bind randomly to the single-stranded sequence of NaOH-treated magnetic beads, and the polymerase continued to synthesize the complementary strand in the 5' to 3' direction of this primer, wherein NNNGGNNNB was a randomly combined sequence.

Figure 4:
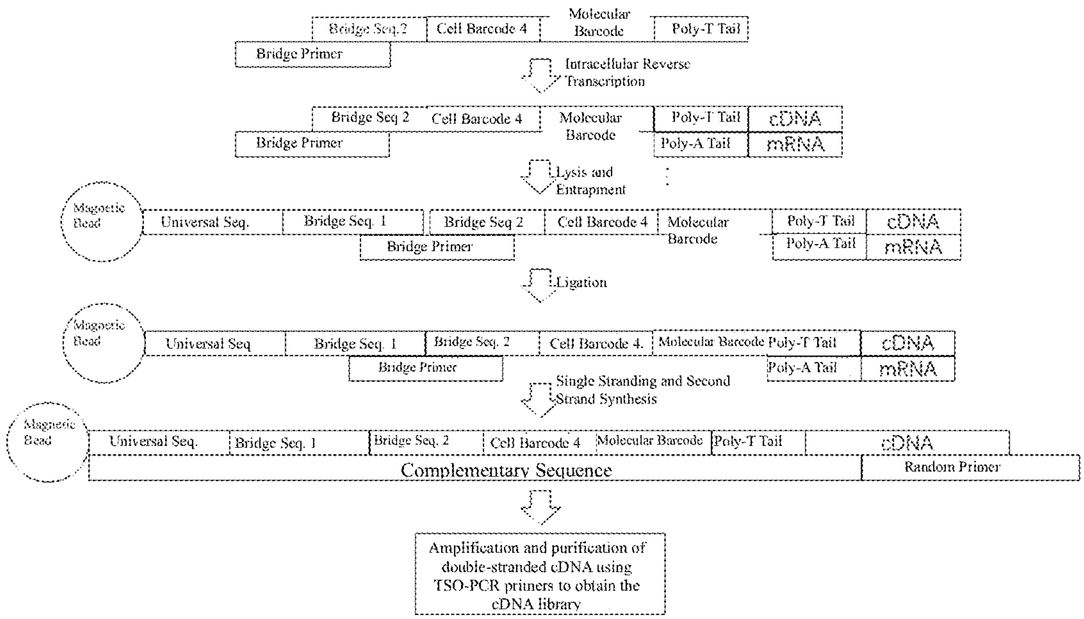
FIG. 4 is a flow chart of cDNA library construction, wherein the universal sequence comprises the Universal Primer Sequence, the Cell Barcode Sequence 1, the Adapter Sequence 1, the Cell Barcode Sequence 2, the Adapter Sequence 2 and the Cell Barcode Sequence 3 of FIG. 2.
Figure 5:
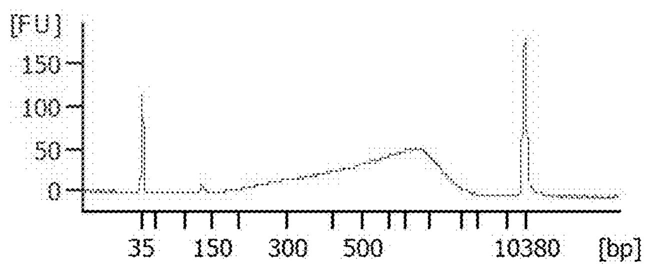
FIG. 5 is a diagram of size distribution of fragments in the prepared cDNA sequencing library.

After the second strand synthesis reaction, the molecular labeled magnetic beads were washed three times on a magnetic rack, the supernatant being aspirated and discarded, and a PCR reagent mix (KAPA HiFi Hot Start Ready Mix 1× and TSO-PCR primer 0.1 μM) was added. Where, the TSO-PCR primer sequence was: 5'-AAGCAGTGGTATCAACGCAGAGT-3'(SEQ ID No. 8). The PCR program was as follows: 98° C. pre-denaturation for 3 min; 98° C. denaturation for 20 sec, 67° C. annealing for 15 sec and 72° C. extension for 6 min, which were repeated for 12 cycles; 72° C. extension for 5 min and 4° C. hold, such that a large amount of labeled cDNA was obtained. Vazyme DNA clean beads were used to purify the PCR products. The DNA clean beads were shaken to mix well and placed at room temperature for at least 30 min prior to use. The purification procedure was as follows:

(1) adding 50 μl of DNA clean beads to the above-mentioned PCR reaction system, and mixing thoroughly by pipette mixing more than 10 times to ensure a homogeneous system; (2) incubating at room temperature for 10 min; (3) placing the PCR tube on a magnetic rack for 5 min to ensure a thorough adsorption of the DNA clean beads; (4) keeping the PCR tube on the magnetic rack and carefully discarding the supernatant; (5) adding 200 μl of freshly prepared 80% ethanol, and incubating for 30 seconds before discarding the supernatant; (6) repeating once the above step; (7) opening the cap and dry in the air for 8 min; (8) adding 13 μl of elution buffer to the PCR tube to cover the DNA clean beads, remove the PCR tube from the magnetic rack and re-suspend the DNA clean beads; (9) incubating at room temperature for 2 min and aspirate 12 μl as the final cDNA library (see FIG. 4 for the detailed workflow of the above reactions); (10) analyzing the fragment size of the cDNA library with Agilent 2100 Bioanalyzer (FIG. 5), the cDNA library fragments obtained being in the range of 300-1000 bp.

Figure 6:
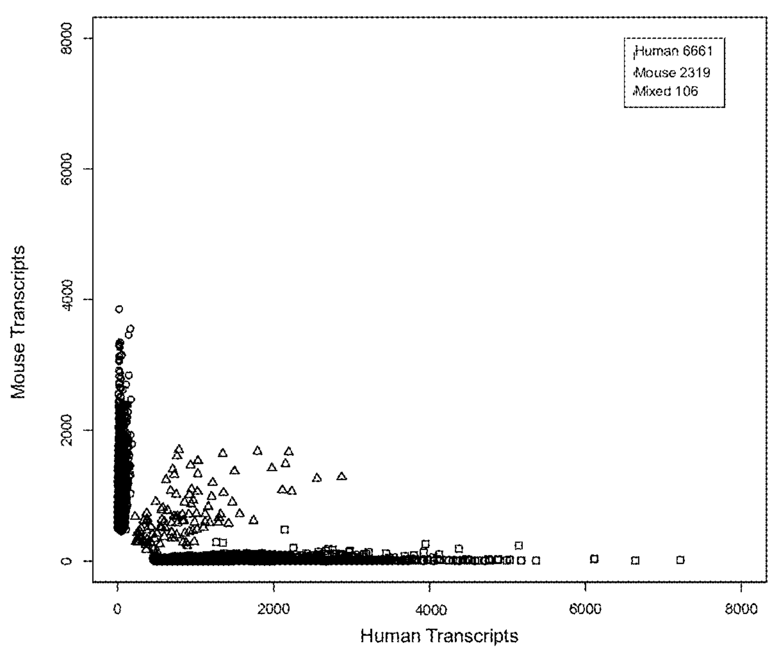
FIG. 6 is a diagram of clustering comparison of mixed human and mouse cells.

The gene sequencing library was constructed using the following cDNA sequencing library construction method, and the constructed gene sequencing library was sent to Hangzhou Repugene Technology Co., Ltd. for sequencing. A gene expression profile was obtained by demultiplexing, screening and comparison of the returned sequencing data. The matrix file was imported for R language analysis such that the matrix data could be converted for visualization. As can be seen from FIG. 6, there was a very small amount of doublet contamination, and a level of high-throughput single cell sequencing can be achieved.

2. Construction of cDNA Sequencing Library.

(1) 5 ng starter DNA fragmentation

Vazyme TD512 kit was used.

(a) The 5×TTBL (TruePrep Tagment Buffer L) was thawed at room temperature, and mixed thoroughly by inversion for use later. The 5×TS (Terminate Solution) was checked to confirm that it was at room temperature and the tube wall was flicked to confirm that there was no precipitation. In the case of precipitation, the Terminate Solution was heated at 37° C. and shaked vigorously to mix thoroughly such that the precipitate dissolves.

(b) Each of the following components was added to a sterile PCR tube in order: 5×TTBL, 4 μl; DNA, 5 ng; TTE Mix V1, 5 μl; and $ddH_2O$ to make up to 20 μl.

(c) The mixture was mixed thoroughly by pipetting gently for 20 times.

(d) The PCR tube was put into a PCR instrument and set the following program: 55° C. 10 min; and 10° C. hold.

(e) 5 μl of the 5×TS was added into the reaction products immediately and mixed thoroughly by gently pipetting up and down. Leave at room temperature for 5 min.

(2) PCR enrichment was conducted.

(a) The sterile PCR tube was put in an ice bath and each of the following components was added in order: $ddH_2O$, 4 μl; products of step 1, 25 μl; 5×TAB, 10 μl; P5 (10 μM), 1 μl; N7XX, 5 μl; and TAE, 1 μl.

The kit TruePrep™ Index Kit V2 for Illumina® (Vazyme #TD202) was used, and the kit manual was referred to for the detailed procedure.

(b) The reactants in the PCR tube were gently pipetted up and down to mix thoroughly, and the PCR tube was put in a PCR instrument for the following program: 72° C. for 3 min, 98° C. pre-denaturation for 30 sec; 98° C. denaturation for 15 sec, 60° C. annealing for 30 sec, and 72° C. extension for 3 min, which were repeated for 11 cycles in total; and hold 4° C.

(3) Size selection and purification of amplification products

AMPure XP magnetic beads were used for size selection and purification. The volume of starter PCR product should be 50 μl. Before the next step, the volume of the starter PCR product was made up to 50 μl with sterile distilled water, for the product volume would be less than 50 μl due to the evaporation of samples during PCR; otherwise unexpected selected size may be obtained. The volume of magnetic beads needed in the 2 rounds (R1 and R2) during selection was as follows:

Volume of AMPure XP magnetic beads in the first round R1=30.0 μl (0.60×), and volume of AMPure XP magnetic beads in the second round R2=7.5 μl (0.15×).

Where, the "×" was calculated from the volume of PCR products, for example, "0.60×" indicates 0.60×50 μl=30.0 μl.

(a) The AMPure XP magnetic beads were mixed thoroughly by vortexing, and pipette R1 volume of the beads into 50 μl of the PCR products. Mix thoroughly by gently pipetting up and down for 10 times. Incubate at room temperature for 5 min.

(b) The tube was spun down briefly and the tube was put on a magnetic rack to separate the AMPure XP magnetic beads and the liquid. The solution was being waited to become clear (approximately 5 min), the supernatant was carefully transferred to a new EP tube and discarded the magnetic beads.

(c) The AMPure XP magnetic beads were mixed thoroughly by vortexing and R2 volume of the beads was pipetted into the supernatant. The supernatant was mixed thoroughly by gently pipetting up and down for 10 times and incubated at room temperature for 5 min.

(d) The tube was spun down briefly and put on a magnetic rack to separate the AMPure XP magnetic beads and the liquid. The solution was being waited until it became clear (approximately 5 min), and the supernatant was discarded carefully.

(e) The EP tube was kept on the magnetic rack at all times. The AMPure XP magnetic beads were rinsed with 200 μl of freshly prepared 80% ethanol. The rinsed AMPure XP magnetic beads were added to the EP tube. The EP tube was incubated at room temperature for 30 sec, and then the supernatant was discarded carefully.

(f) The step 5 was repeated such as to rinse twice in total.

(g) The EP tube was kept on the magnetic rack at all times, open the cap and air-dry the AMPure XP magnetic beads for 10 min.

(h) The EP tube was taken off the magnetic rack, and eluted with 13 μl of sterile ultrapure water. The reactants in the EP tube were mixed thoroughly by vortexing or gently pipetting. The tube was briefly spun down and put on a magnetic rack to separate the AMPure XP magnetic beads and the liquid. The operator waited until the solution becomes clear (approximately 5 min), pipetted carefully 12 μl of the supernatant into a sterile EP tube to obtain the sequencing library. The sequencing library can be stored at −20° C.

Embodiment 3

Optimization of Lysis Buffer of Different Formulations.

Figure 7:
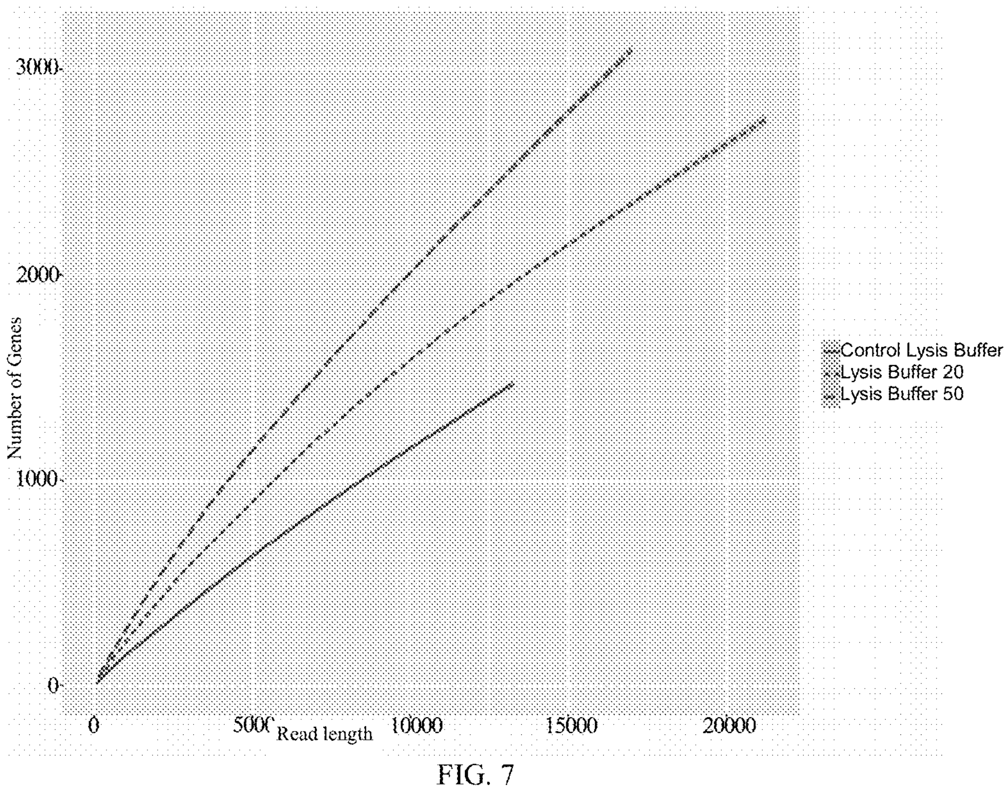
FIG. 7 is a diagram of read length against number of genes for comparison of sequencing with different lysis buffers.

As in Embodiment 2, after loading cells carrying molecular labels on the microwell plate, excess molecular labeled magnetic beads were washed away with DPBS solution, and lysis buffer of three different formulations were added into three microwell plates, respectively, the 3 lysis buffers in turn including: control lysis buffer (0.1 M Tris-HCl pH 7.5, 0.5 M LiCl, 1% SDS, 10 mM EDTA and 5 mM dithiothreitol), lysis buffer 20 ($ddH_2O$, 1% SDS, 20% formamide and 3×SSC) and lysis buffer 50 ($ddH_2O$, 1% SDS, 50% formamide and 3×SSC), followed by incubating for 30 min for sufficient lysis. The steps thereafter were the same as in Embodiments 2. Among the components, SDS played a major role in lysis, formamide facilitated hybridization of nucleic acid molecules, and SSC assisted in enhancing hybridization efficiency. The constructed gene sequencing library was sent to Hangzhou Repugene Technology Co., Ltd. for sequencing with the HiSeq2500PE125 sequencing strategy. As shown by the analysis of the sequencing results, lysis buffer 50 significantly improved the number of cells with UMI of greater than 500 as well as the average number of gens (FIG. 7), substantially improving the reaction efficiency of the platform.

Embodiment 4

Analysis of Mouse Testicular Cells.

Figure 8:
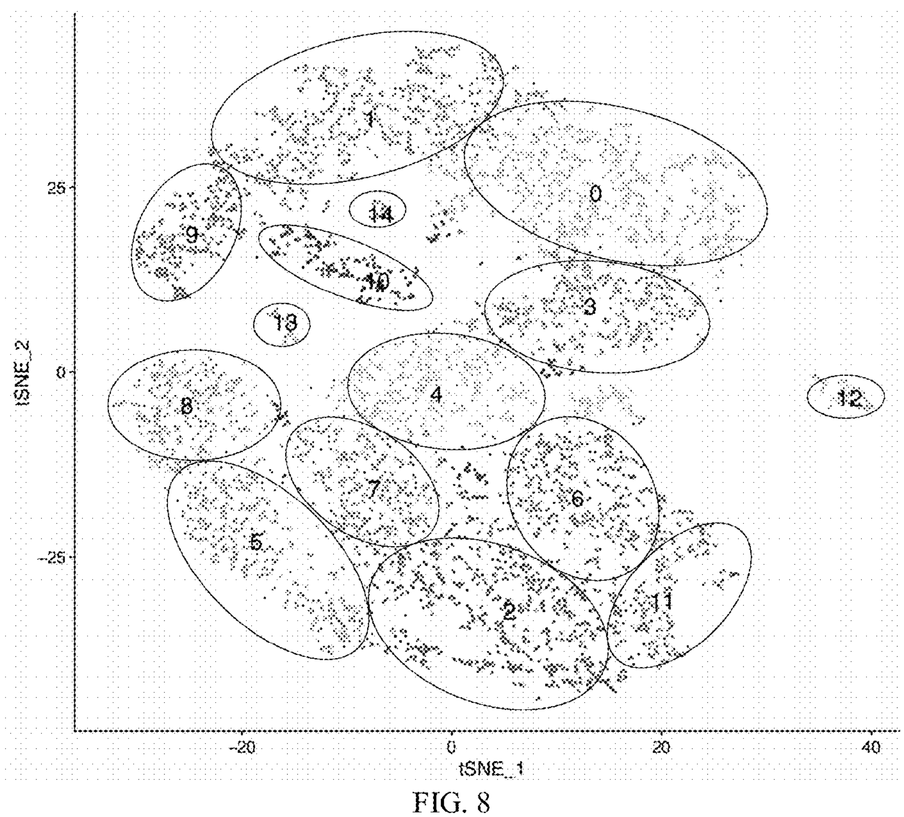
FIG. 8 depicts tSNE analysis result of mouse testicular cells.

Five million detached mouse cells were employed for library construction and obtaining a sequencing library according to the procedure in Embodiment 2. The constructed gene sequencing library was sent to Hangzhou Repugene Technology Co., Ltd. for sequencing with the HiSeq2500PE125 sequencing strategy. A gene expression profile was obtained by demultiplexing, screening and comparison of the returned sequencing data. The matrix file was imported into R for analysis such that the matrix data could be converted for visualization. FIG. 8 shows the result of tSNE analysis of mouse testicular cells, demonstrating that mouse testes can be divided into 14 subpopulations.

Embodiment 5

The present invention can also be used for microfluidics-based single cell sequencing platforms. After obtaining fixed cells carrying one round of cell barcode by using the method of Embodiment 2, Chromium Chip E by 10× Genomics (10×Genomics #2000121) was used for reactions. Inlet 1 was injected with 75 μl of fixed cells mixed with the ligation system (10 μl of cells, 50.5 μl of enzyme-free water, 7.5 μl of T4 Ligation Buffer, 3 μl of T4 ligase, 1.5 μl of 10× Reducing Agent B and 2.5 μl of 100 mM Bridge Primer); inlet 2 was injected with 40 μl of single cell ATAC gel microbeads containing the Lysis Buffer (10×Genomics #2000132, the microbead sequence as described in Embodiment 1); and inlet 3 was injected with 240 μl of Partitioning Oil (10×Genomics #220088). Then the emulsion-coated microbeads were incubated at 37° C. for 1.5 hours to allow for a sufficient ligation reaction. After the reaction, the microbeads were collected and subjected to exonucleolytic cleavage, single-stranding and second strand synthesis reactions according to the protocol described in Embodiment 2, and finally the cDNA library was obtained by PCR amplification and purification.

Embodiment 6

Assay for Transposase-Accessible Chromatin Ultra-High-Throughput Single Cell Sequencing.

Annealing of the labeled magnetic beads in Embodiment 1 and the bridge primer was executed. The magnetic beads and the bridge primer (bridge primer sequence: 5'-CGTCGTGTAGG-GAAAGTGTGACGCTGCCGACGA-3') (SEQ ID No. 9) were mixed thoroughly and subjected to gradient annealing to form sticky ends. Sequences which did not bind to the bridge primer were resected using the exonuclease EXO I. After the resection, the beads were washed once with 150 μl of TE-SDS and TE-TW, and finally resuspended with TE-TW and stored at 4° C. for use later.

(1) Preparation of Specific Molecular Barcode Transposase-Embedded Complex

The naked Tn5 transposase was purchased from Nanjing Vazyme Biotech Co. Ltd. The transposase and the embedment buffer were provided by the (Vazyme) Tn5 Transposome (S111) kit produced by Nanjing Vazyme Biotech Co. Ltd.

(1) See Table 2 hereinafter for the embedment sequence.

TABLE 2

| | |
|---|---|
| P7 adapter segment | GTCTCGTGGGCTCGGAGATGTGTATAAGAGACAG (SEQ ID No. 10) |
| Specific barcode segment | ACACTCTTTCCCTACACGACGNNNNNNNNNNAGATGTGTATAAGAGACAG (SEQ ID No. 11) |
| Mosaic Ends segment | CTGTCTCTTATACACATCT (SEQ ID No. 12) |

Wherein, the specific molecular barcode 10×N included in the specific barcode segment was the core sequence of the cell barcode sequence, this core sequence corresponding to each Tn5 complex being different, and since there were four options of A/T/C/G for each site, there were $4^{10}$ options for the 10×N sequence. N represents any one of A/T/C/G and was randomly synthesized.

Figure 9:
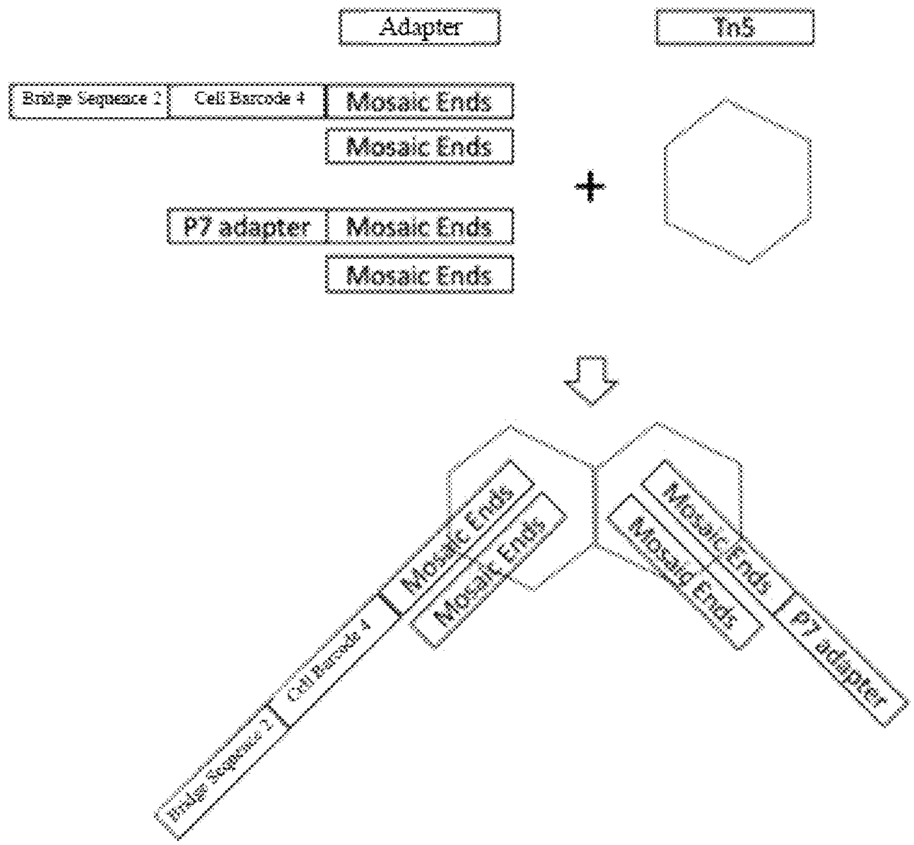
FIG. 9 depicts the adapter embedment of adapter sequences with Tn5 transposase, wherein the two adapter sequences comprise a specific molecular barcode sequence and a universal sequence, respectively, and a Tn5-embedded complex is produced by incubation of the adapter sequences with naked Tn5 transposase, a single Tn5-embedded complex carrying both of the specific molecular barcode sequence and the universal sequence.

(2) 96 types of oligonucleotide sequences with specific molecular barcode were annealed (annealing of P7 adapter segment+Mosaic Ends segment produced the universal sequence, i.e., the P7 Adapter—Mosaic Ends/Mosaic Ends of the adapter in FIG. 9; annealing of the specific barcode segment+Mosaic Ends segment produced a specific molecular barcode sequence, i.e., the Bridge Sequence 2—Cell Barcode 4—Mosaic Ends/Mosaic Ends in FIG. 9). Each well of the 96 wells was loaded with 2 types of embedment segments, comprising the P7 adapter segment+Mosaic Ends segment shared by all wells, and the specific barcode segment+Mosaic Ends segment which was specific between wells.

(3) The naked Tn5 enzyme and the embedment buffer were added evenly to a 96-well plate, and then crytopreservation buffers of the 96 types of barcode adapters from step (2) were added into each well, pipetted up and down for 5 times and incubated at 30° C. for 1 hour, followed by storage in a −20° C. freezer (FIG. 9).

2. Nuclei Extraction from Fresh Tissues

Fifty mg of a fresh tissue sample was ground into powder with liquid nitrogen and quickly transferred to a pre-chilled 1.5 ml EP tube. The sample was resuspended in 1 ml of the lysis buffer ($ddH_2O$, 10 mM Tris-HCl pH 7.4, 10 mM NaCl, 3 mM $MgCl_2$, 1% BSA, 0.1% Tween-20, 0.1% IGEPAL CA-630 and 0.01% digitonin) and lysed on ice for 3 min. The lysed sample was resuspended with RSBT buffer ($ddH_2O$, 10 mM Tris-HCl pH 7.4, 10 mM NaCl, 3 mM $MgCl_2$, 1% BSA and 0.1% Tween-20), and filtered to remove the tissue residue. The nuclei were fixed with 1% formaldehyde at room temperature for 10 min. The fixation and crosslinking was terminated with glycine. The crytopreservation buffer ($ddH_2O$, 50 mM Tris-HCl pH 8.0, 25% glycerol, 5 mM $Mg(OAc)_2$ and 0.1 mM EDTA) was prepared. The nuclei were resuspended with 975 μl of the crytopreservation buffer, 5 μl of 5 mM DTT and 20 μl of 50× protease inhibitor cocktail, following which the nuclei can be crytopreserved at −80° C. Alternatively, the nuclei could be suspended in 1 ml of RSBT buffer, filtered and counted for use later. For resuscitation of the crytopreserved sample, the sample was taken out and put in an oven to thaw at 37° C. for 2 min, centrifuged at 500 g/5 min with the supernatant being discarded, resuspended in 200 μl of the lysis buffer, and put on ice for 3 min. And the sample was washed with RSBT, filtered and counted for use later.

3. Nuclei Extraction from Mixed Human 293T and Mouse 3T3 Cells

Two million each of mouse fibroblast cells (3T3) and human embryonic kidney cells (293T) were mixed thoroughly and washed once with PBS, then transferred to an 1.5 ml EP tube and subsequently resuspended with 1 ml of the lysis buffer ($ddH_2O$, 10 mM Tris-HCl pH 7.4, 10 mM NaCl, 3 mM $MgCl_2$ 1% BSA, 0.1% Tween-20, 0.1% IGEPAL CA-630, 0.01% digitonin) and lysed on ice for 3 min. The lysed sample was wash twice with the RSBT buffer ($ddH_2O$, 10 mM Tris-HCl pH 7.4, 10 mM NaCl, 3 mM $MgCl_2$, 1% BSA and 0.1% Tween-20). The nuclei were fixed with 1% formaldehyde at room temperature for 10 min. The fixation and crosslinking was terminated with glycine. The crytopreservation buffer ($ddH_2O$, 50 mM Tris-HCl pH 8.0, 25% glycerol, 5 mM $Mg(OAc)_2$ and 0.1 mM EDTA) was prepared. The nuclei were resuspended with 975 μl of the crytopreservation buffer, 5 μl of 5 mM DTT and 20 μl of 50× protease inhibitor cocktail, following which the nuclei can be crytopreserved at −80° C. Alternatively, the nuclei could be suspended in 1 ml of the RSBT buffer, filtered and counted for use later. For resuscitation of the crytopreserved sample, the sample was taken out and put in an oven to thaw at 37° C. for 2 min, centrifuged at 500 g/5 min with the supernatant being discarded, resuspended in 200 μl of the lysis buffer, and put on ice for 3 min. And the sample was washed with RSBT, filtered and counted for use later.

4. Tn5 Pre-Labelling of Mixed Human 293T and Mouse 3T3 Cells

The prepared nuclei were resuspended in 1 ml of RSBT, filtered and counted. The 2×TD buffer ($ddH_2O$, 20 mM Tris-HCl pH7.6, 10 mM $MgCl_2$, 20% dimethylformamide) was prepared. The tagmentation buffer (22.5 μl per well, comprising 12.5 μl of 2×TD buffer, 9.5 μl of 1×DPBS, 0.25 μl of 1% digitonin, and 0.25 μl of 10% Tween-20) was prepared. The nuclei were resuspended in the tagmentation buffer, and dispensed into a 96-well plate with approximately 10,000 nuclei per well. The transposase-embedded complex of Embodiment 3 was added into the 96-well plate containing the nuclei at 2.5 μl per well, and placed at 55° C. to react for 30 min. After the reaction, 25 μl of the 2× Terminate Solution (25 ml of 40 mM EDTA and 3.9 μl of 6.4 M Spermidine) was added to each well and left to stand still at 37° C. for 15 min. The liquid was collected and mixed in a 15 ml centrifuge tube, spun down at 500 g/5 min with the supernatant being discarded, and washed once with 1 ml of RSBT. The nuclei were counted and dispensed into a 1.5 ml EP tube at 500,000 nuclei per tube, and resuspended in 20 μl of RSBT, followed by addition of 30 μl of PNK reaction solution (5 μl of 10×PNK buffer, 5 μl of 10 mM ATP, 10 μl of $ddH_2O$ and 10 μl of PNK enzyme) and incubation at 37° C. for 30 min, and then centrifuged when the reaction was completed, the supernatant being discarded. The sample was washed twice with RSBT and then put on ice for use later.

5. Microwell Plate ATAC Sequencing of Mixed Human 293T and Mouse 3T3 Cells

The Tn5-labeled nuclei were employed. The nuclei suspension was dripped into a microwell plate, and briefly centrifuged such that 80-90% of the nuclei were loaded in the microwells, with each well capturing 0-10 nuclei. Cellular DNA fragments within the same well were distinguished by the Cell Barcode 4 on Tn5. The bridge primer and the labeled magnetic beads were annealed such that the sticky ends were formed on fragments on the labeled magnetic beads. 200,000 molecular labeled magnetic beads were added to the nuclei-captured microwell plate, and the plate was put on a magnet and mixed well gently so that the magnetic beads covered more than 99% of the microwells. The excess molecular labeled magnetic beads were washed away with RSBT solution. 200 μl of the lysis buffer (100 μl of 10% SDS, 40 μl of proteinase K, 100 μl of 10×T4 buffer, 200 μl of 50% PEG 8000 (mass volume ratio) and 560 μl of 10 mM Tris-HCl pH 8.0) was dripped slowly into the microwell plate covered with magnetic beads, followed by lysis incubation at room temperature for 30 min to allow sufficient complementary hybridization of the bridge sequence on the magnetic beads and the bridge primers on the nuclei. After incubation, the microwell plate was inverted onto a magnet, and magnetic beads carrying molecular label-DNA complex were collected, transferred to a 1.5 ml EP tube and washed twice with 6×SSC, and then washed once again with 50 mM Tris pH8.0.; 50 μl of ligation mix (2 μl of T4 ligase, 5 μl of T4 buffer, 2 μl of dNTP, 10 μl of 50% PEG8000 (mass volume ratio) and 31 μl of $ddH_2O$) was added to the EP tube containing the molecular labeled magnetic beads, and reacted at 25° C. for 1.5 h. After the ligation reaction, the molecular labeled magnetic beads were washed once with TE-SDS, TE-TW and 10 mM Tris pH8.0, respectively, on a magnetic rack, and then the magnetic beads were suspended in 100 μl of an extension system (20 μl of 5×RT buffer, 10 μl of dNTP, 2.5 μl of Klenow polymerase, 20 μl of 50% PEG (mass volume ratio) and 47.5 μl of $ddH_2O$), and reacted at 37° C. for 1 hour. After the reaction, the molecular labeled magnetic beads were washed once with TE-SDS, TE-TW and 10 mM Tris pH8.0, respectively on a magnetic rack. The magnetic beads were suspended in 500 μl of 0.1 M NaOH and incubated at room temperature for 5 min for single stranding. Then the beads were washed twice with TE-TW and washed once with 10 mM Tris pH8.0. The target segment was enriched from the magnetic beads with the primers index P5 and index P7, and the PCR products were purified with Vazyme DNA clean beads to obtain products of 300-500 bp.

Figure 10:
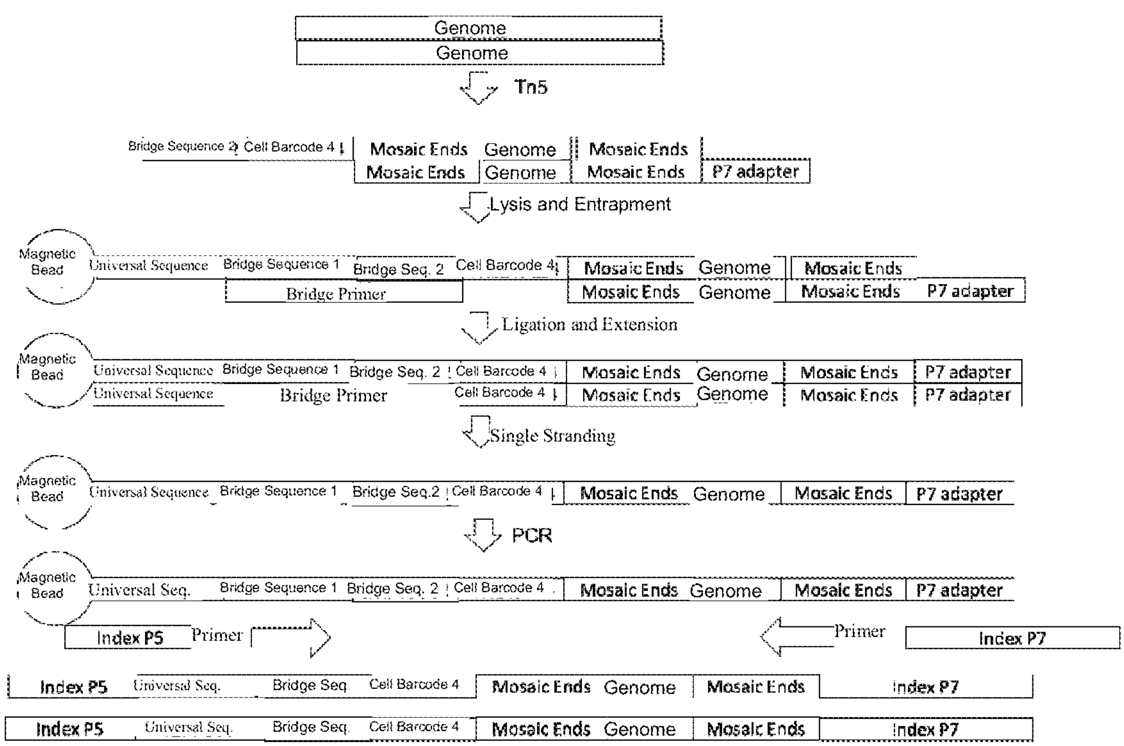
FIG. 10 is a flow chart of ATAC library construction, wherein the universal sequence comprises the Universal Primer Sequence, the Cell Barcode Sequence 1, the Adapter Sequence 1, the Cell Barcode Sequence 2, the Adapter Sequence 2 and the Cell Barcode Sequence 3 of FIG. 1; and the bridge sequence comprises the Bridge Sequence 1 and the Bridge Sequence 2.
Figure 11:
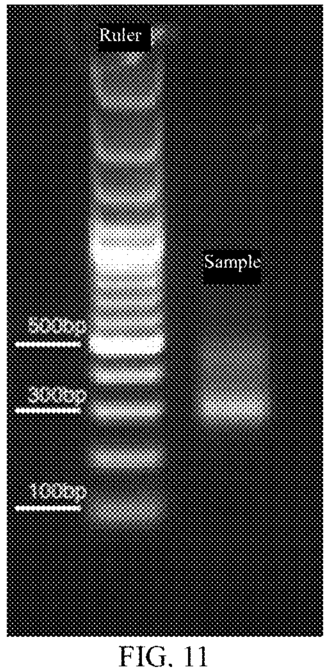
FIG. 11 is a diagram of size distribution of the fragments in the prepared gene sequencing library.
Figure 12:
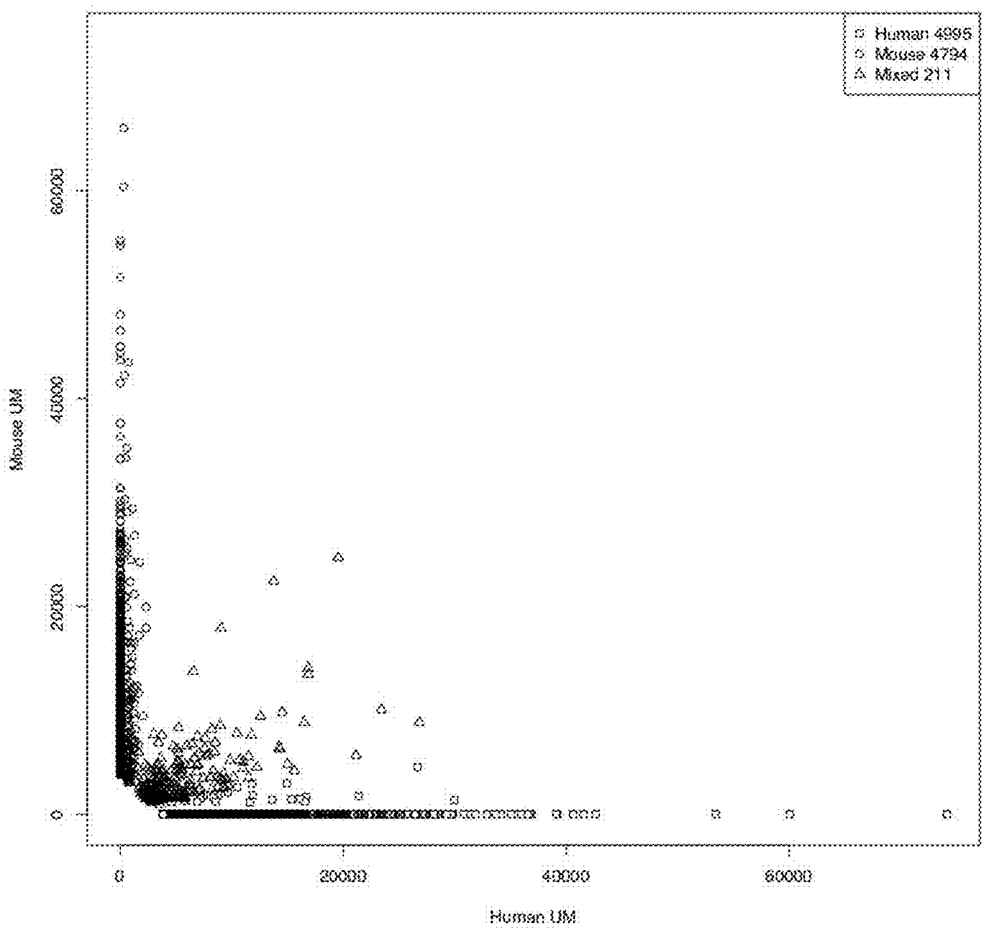
FIG. 12 is a diagram of clustering comparison of mixed human and mouse cells.
Figure 13:
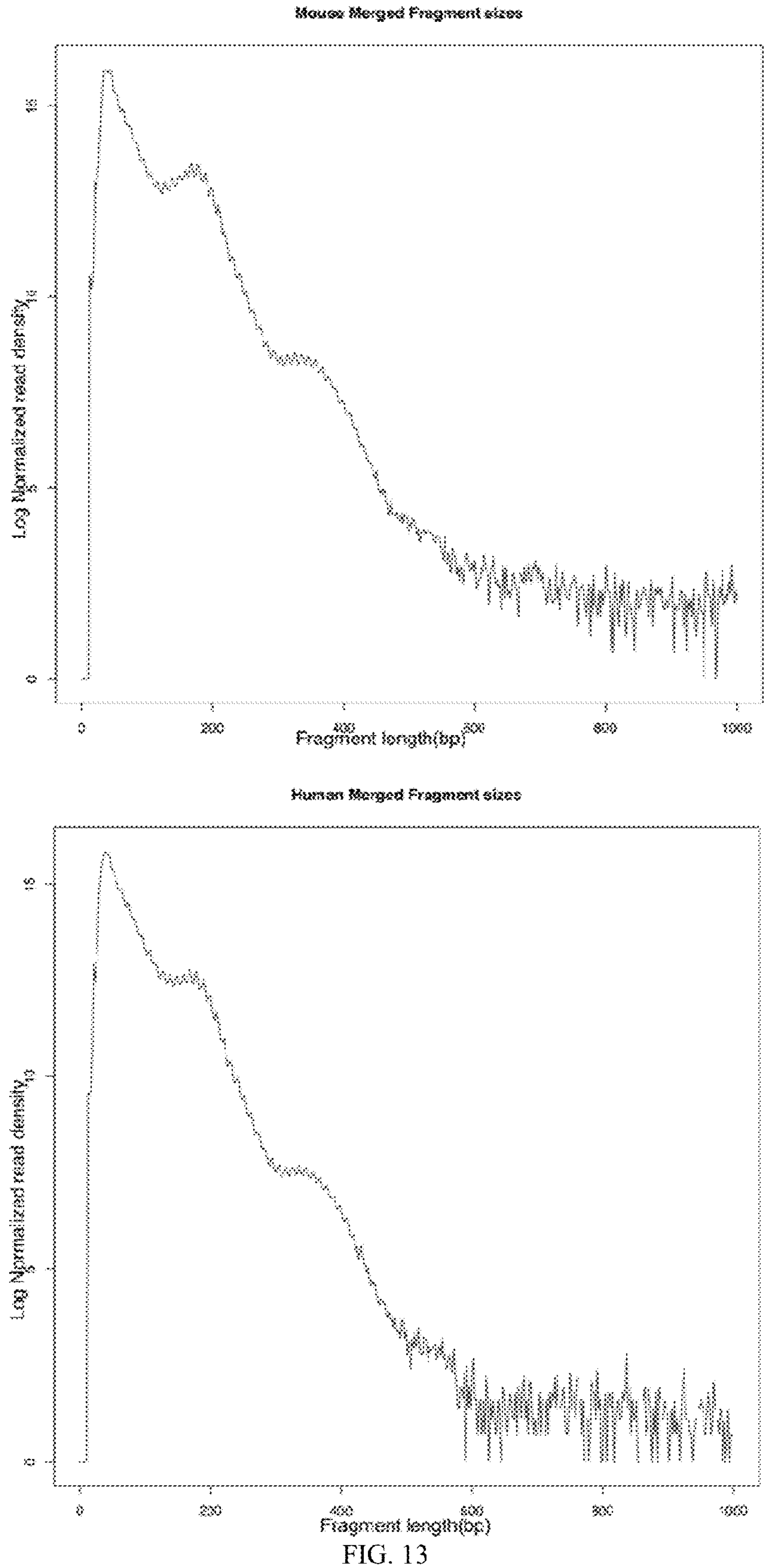
FIG. 13 depicts size distribution of DNA fragments of the human sample and the mouse sample.
Figure 14:
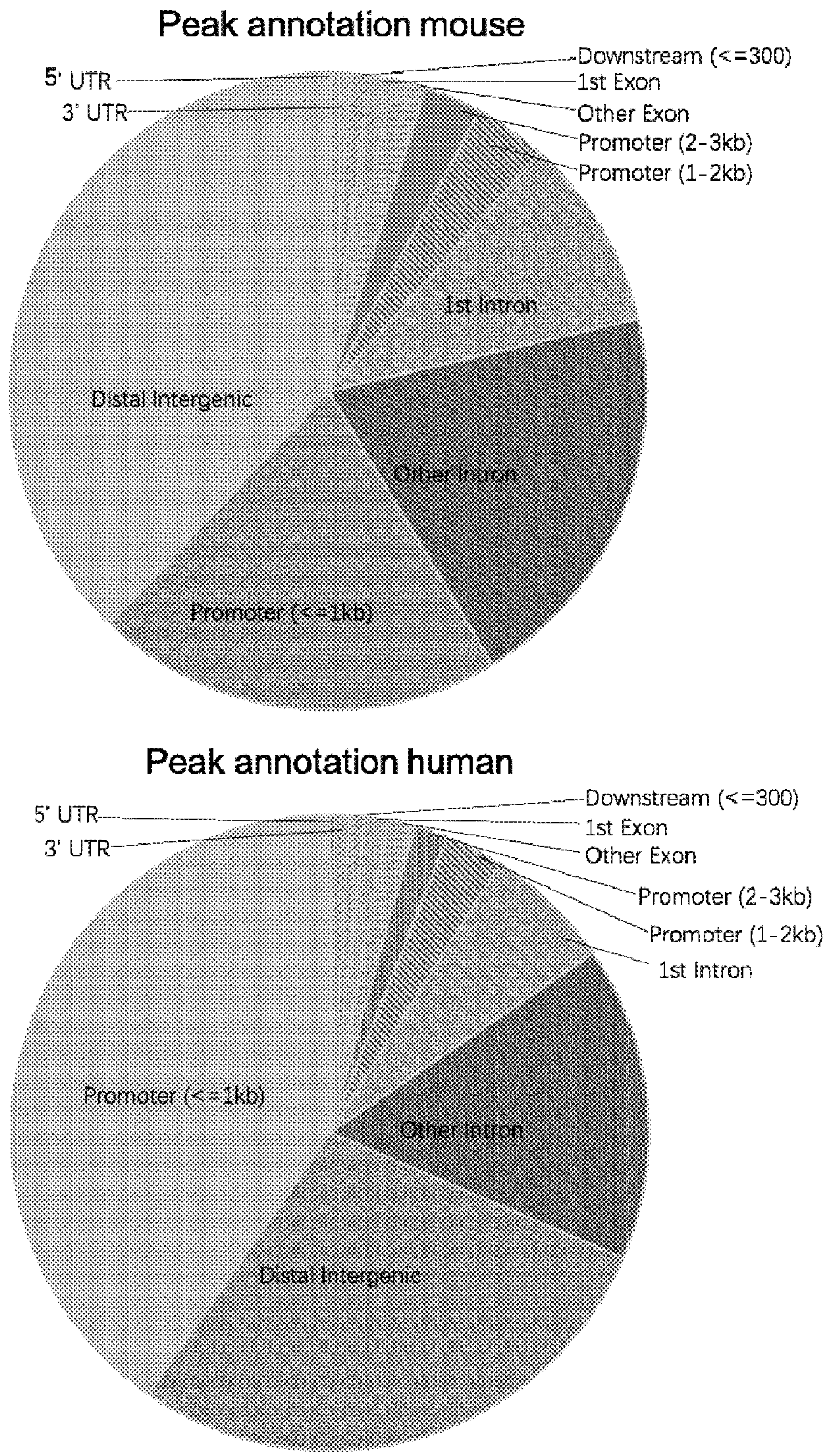
FIG. 14 are peak annotation distribution diagrams for the mouse sample and the human sample.
Figure 15:
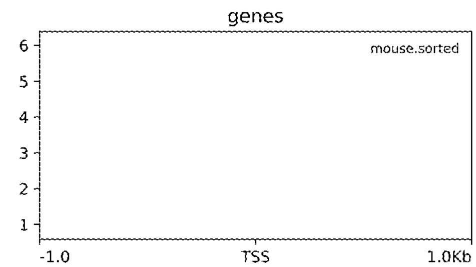
FIG. 15 is a mouse TSS enrichment diagram.
Figure 16:
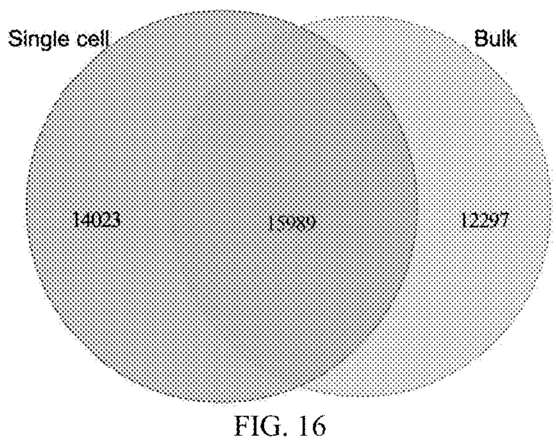
FIG. 16 depicts the overlapping-peak distribution for mouse single-cell ATAC and bulk ATAC.
Figure 17:
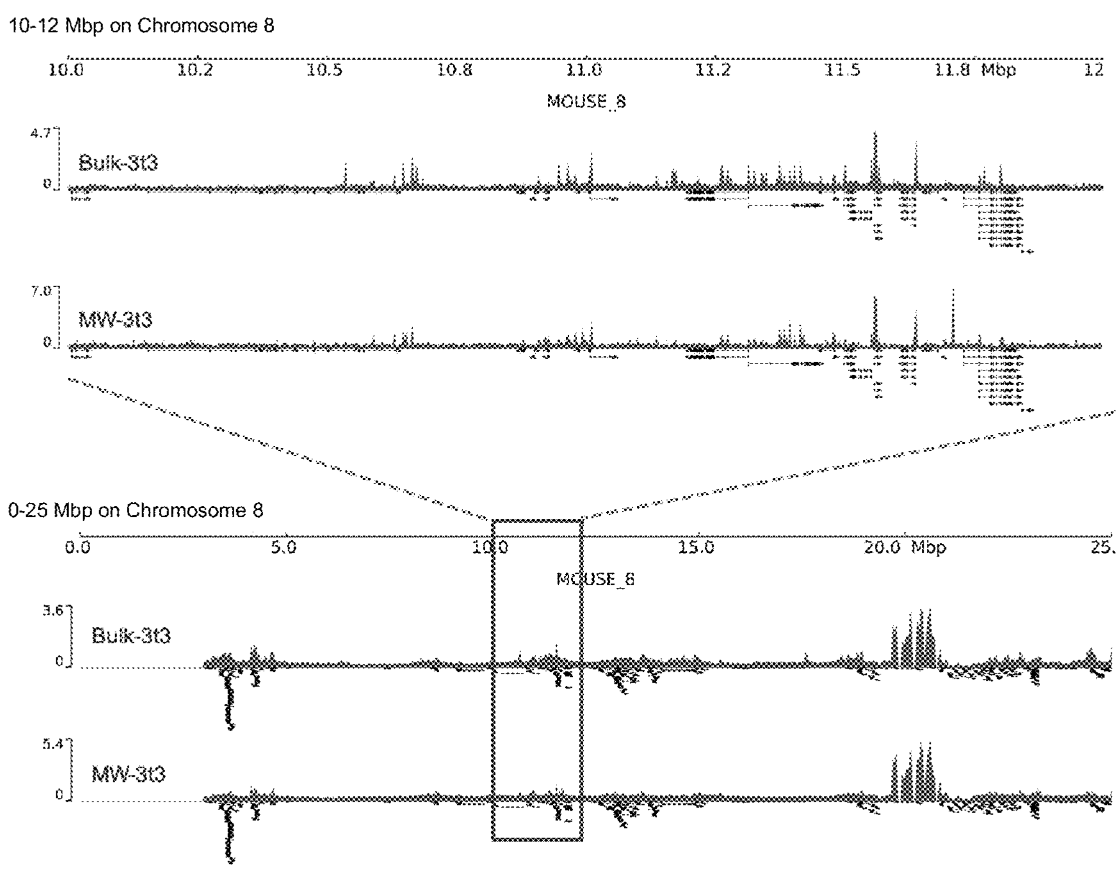
FIG. 17 is a diagram for comparison of the distribution of reads at 0-25 Mbp on chromosome 8 for mouse single cell ATAC and bulk ATAC.

The detailed workflow of the above reactions is shown in FIG. 10. As shown in FIG. 11, the library size was distributed around 300-500 bp.

The gene sequencing library was constructed using the method above, and the constructed gene sequencing library was sequenced with an MGI/Illumina Next Gen Sequencing instrument. A cell by peak matrix was obtained by demultiplexing, screening and comparison of the returned sequencing data. The matrix file was imported into R for analysis such that the matrix data could be converted for visualization. Figures. 12-17 indicated a very small amount of doublet contamination (FIG. 12), expected fragment size (FIG. 13), normal peek distribution (FIG. 14), enrichment at the TSS (FIG. 15), peak distribution of bulk and single-cell ATAC for mouse 3T3 cells (FIGS. 16 and 17), and that the sequencing quality could reach the level of single-cell ATAC high-throughput sequencing.

The sequences of primers for library construction are shown in Table 3 hereinafter. Where, N represents any one of A/T/C/G and was randomly synthesized. S denotes a thio modification of the terminal base to improve the terminal base stability.

TABLE 3

| | |
|---|---|
| index P5 | 5'phos-GAACGACATGGCTACGATCCGACTTGCC TGTCCGCGGAAGCAGTGGTATCAACGCAGAGTA-s-C-s-G-3' (SEQ ID No. 13) |
| index P7 | TGTGAGCCAAGGAGTTGTTGTCTTCNNNNNNNNNN GTCTCGTGGGCTCGG (SEQ ID No. 14) |

Embodiment 7

The assay for transposase-accessible chromatin ultra-high-throughput single cell sequencing of the present invention can also be used for microfluidics-based single cell sequencing platforms. After obtaining fixed cells carrying one round of cell barcode by using the method of Embodiment 6, Chromium Chip E by 10×Genomics (10×Genomics #2000121) was used for reactions. Inlet 1 was injected with 75 μl of fixed cells mixed with the ligation system (10 μl of cells, 50.5 μl of enzyme-free water, 7.5 μl of T4 ligation buffer, 3 μl of T4 ligase, 1.5 μl of 10× Reducing Agent B and 2.5 μl of 100 mM bridge primer); inlet 2 was injected with 40 μl of single cell ATAC gel microbeads containing the lysis buffer (10×Genomics #2000132, microbead sequence as described in Embodiment 1); and inlet 3 was injected with 240 μl of Partitioning Oil (10×Genomics #220088). Next, the emulsion-coated microbeads were incubated at 37° C. for 1.5 hours to allow for a sufficient ligation reaction. After the reaction, the microbeads were collected and subjected to exonucleolytic cleavage, single stranding and second strand synthesis reactions according to the protocol described in Embodiment 7, and finally the gene sequencing library for sequencing and bioinformatic analysis was obtained by PCR amplification and purification. Sequencing and bioinformatic analysis of the gene sequencing library was carried out according to the workflow in Embodiment 7.

Embodiment 8

The assay for transposase-accessible chromatin ultra-high-throughput single cell sequencing of the present invention can also be used for Tn5 embedment method with both ends labeled.

Embedment was executed according to method of Embodiment 6 except that each well of the 96 wells comprised 1 embedment fragment, i.e. the specific barcode segment+Mosaic Ends segment specific between wells, and annealing of the specific barcode segment+Mosaic Ends segment produced a specific molecular barcode sequence, i.e., the Bridge Sequence 2—Cell Barcode 4—Mosaic Ends/Mosaic Ends in FIG. 9.

Figure 18:
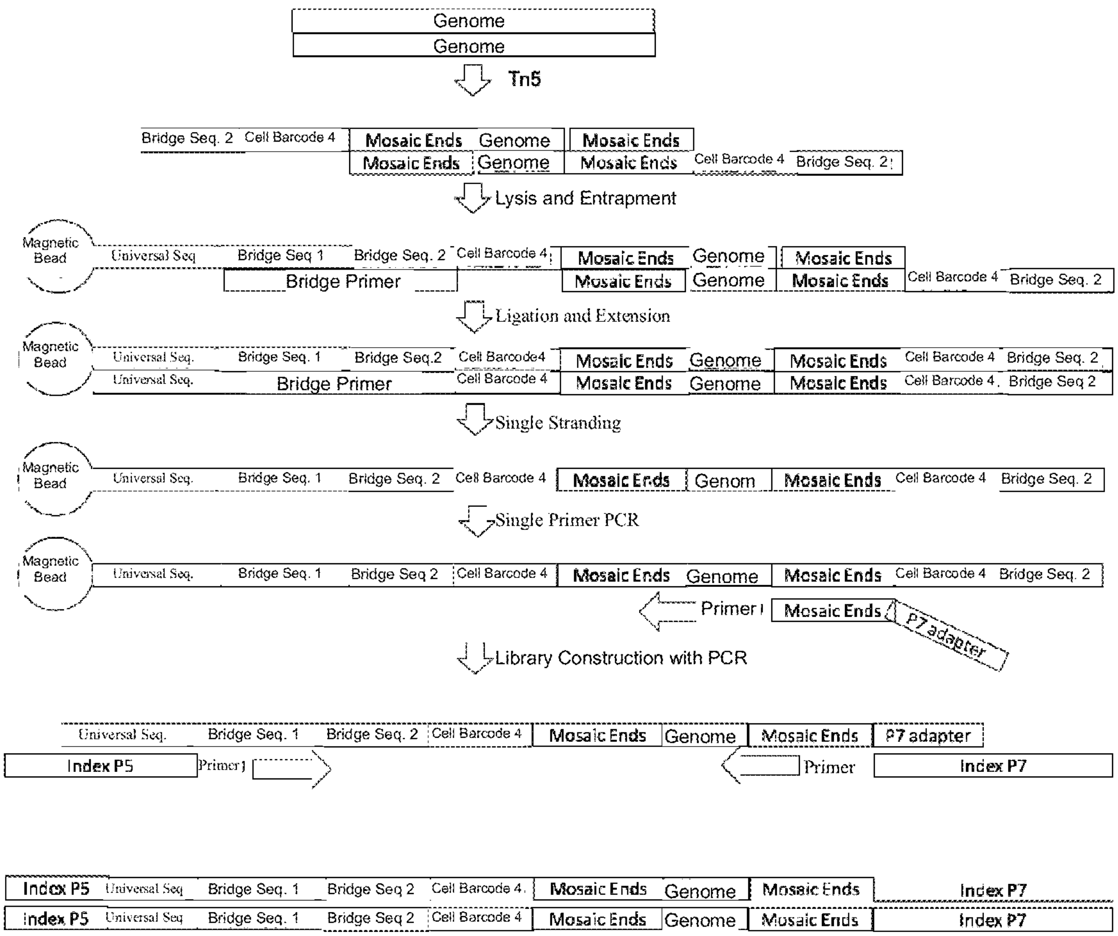
FIG. 18 is a flow chart of ATAC library construction by Tn5 embedment method with both ends being labeled, wherein the universal sequence comprises the Universal Primer Sequence, the Cell Barcode Sequence 1, the Adapter Sequence 1, the Cell Barcode Sequence 2, the Adapter Sequence 2 and the Cell Barcode Sequence 3 of FIG. 1.

Next, the nuclei were labeled according to the protocol in Embodiment 6, and the labeled nuclei were captured on a microwell plate, ligated and extended. 500 μl of 0.1M NaOH solution was added to treat the nuclei for 5 minutes for single stranding, then the P7 adapter—Mosaic Ends primer (i.e. the primer comprising the sequences of P7 adapter and Mosaic Ends fragments) was added for extension After completion of extension, single-stranded products in the supernatant were collected through high-temperature denaturation and the magnetic beads were removed. The gene sequencing library was obtained by PCR amplification and purification with primers index P5 and index P7 (FIG. 18). Sequencing and bioinformatic analysis of the gene sequencing library was carried out according to the workflow in Embodiment 7.

The invention claimed is:

1. An ultra-high-throughput single cell sequencing method comprising the following steps:

(1) preparing following reagents:

a) molecular labeled microbeads, the molecular labeled microbead comprising a microbead body and a coupled molecular label sequence, the molecular label sequence comprising in sequence:

a universal primer sequence, serving as a primer binding region during PCR amplification;

a first cell barcode sequence; and a first bridge sequence;

b) a reverse transcription sequence for intracellular reverse transcription, the reverse transcription sequence comprising in sequence:

a second bridge sequence;

a second cell barcode sequence, forming a cell barcode sequence in conjunction with the first cell barcode sequence, the cell barcode sequence being used for identifying a cell from which an mRNA to which each sequence in a constructed sequencing library corresponds is derived;

a molecular barcode sequence for identifying mRNA to which each sequence in a constructed sequencing library corresponds;

a poly-T tail for complementary pairing with intracellular mRNA with a poly-A sequence; and c) a bridge primer for ligating the above-mentioned label sequence in a) and the reverse transcription sequence in b), the bridge primer having, on both ends, a sequence complementary to the first bridge sequence and the second bridge sequence, respectively;

(2) adding the reverse transcription sequence to a cell sample to be sequenced for intracellular reverse transcription such that the poly-T tail of the reverse transcription sequence is ligated with a cDNA sequence derived from reverse transcription of the intracellular mRNA sequence to obtain a reverse transcription sequence-cDNA sequence;

(3) compartmentalizing one or more of the intracellularly reverse-transcribed cells from step (2) with one molecular labeled microbead by microwell-plate technology or microfluidic technology, and lysing the cells under the action of a lysis buffer, incubating, and then ligating the first bridge sequence with the second bridge sequence by the pairing of bridge primers with the first bridge sequence and the second bridge sequence, respectively, followed by ligation through a ligase, such that a molecular label sequence-reverse transcription sequence-cDNA sequence coupled to the microbead is obtained;

(4) collecting the microbeads coupled with the molecular label sequence-reverse transcription sequence-cDNA sequence, and performing PCR amplification to obtain a cDNA sequence having the first cell barcode sequence, the second cell barcode sequence and the molecular barcode sequence; and (5) constructing a cDNA sequencing library with the product obtained from step (4), and then performing high-throughput sequencing to obtain information of specific transcriptome of millions of single cells;

wherein, the preparation method of the molecular labeled microbeads comprises the following steps:

classifying the bridge primers for synthesizing the molecular label sequences into a plurality of primers in accordance with a number of specific fragments, each primer comprising a specific fragment, there being adapter sequences between each of the primers for bridging, ligation and complementing each other, wherein a primer corresponding to a 5' end of the molecular label sequence further comprises the universal primer sequence, and a primer corresponding to a 3' end of the molecular label sequence further comprises the first bridge sequence; and coupling the primer corresponding to the 5' end of the molecular label sequence to the microbead body, then annealing and extending remaining primers in sequence by PCR, and cascading remaining specific fragments of the molecular label sequence in sequence from the 5' end to the 3' end to prepare and obtain the molecular labeled microbead; and wherein, the molecular label sequence is: 5'-TTTAGG-GATAACAGGGTAATAAGCAGTGGTAT-CAACGCAGAGTACGTNNNNNN CGACTCACTA-CAGGGNNNNNNTCGGTGACACGATC GNNNNNNTCGTCGGCAG CGTC-3' (SEQ ID No. 4), wherein, N represents any one of A/T/C/G and is randomly synthesized.

2. The ultra-high-throughput single cell sequencing method according to claim 1, wherein, the microbead is coupled to the molecular label sequence in such a way comprising: replacing a hydroxyl group with an amine group at C6 position of a nucleotide at the 5' end of the molecular label sequence, having the surface of the microbead modified with a carboxyl group, and coupling through condensation of an amino group and the carboxyl group.

3. The ultra-high-throughput single cell sequencing method according to claim 1, wherein, the first cell barcode sequence comprises a plurality of specific fragments, and the second cell barcode sequence comprises at least one specific fragment, the specific fragments at different locations being selected from the same or different libraries of specific fragments, and the first cell barcode sequence and the second cell barcode sequence identifying cells by using different combinations and arrangements of the specific fragments.

4. The ultra-high-throughput single cell sequencing method according to claim 1, wherein, the cell sample to be sequenced comprises 2 or more types of cells.

5. The ultra-high-throughput single cell sequencing method according to claim 1, wherein, the microbead body is a magnetic microbead;

the intracellularly reverse transcribed cells or transposed nuclei are added to a microwell plate, followed by the addition of the molecular labeled microbead, the microwell in the microwell plate having a diameter big enough to just accommodate one molecular labeled microbead and one or more cells or nuclei; and the capture rate of cells or nuclei in the microwell plate is maintained at over 80%; and the capture rate of the molecular labeled microbead in the microwell plate is over 99%.

6. The ultra-high-throughput single cell sequencing method according to claim 5, wherein, the microwell depth in the microwell plate is 30-160 μm and the microwell diameter is 20-150 μm; and the diameter of the microbead body is 20-145 μm.

7. The ultra-high-throughput single cell sequencing method according to claim 5, wherein, the preparation method of the microwell plate is:

(1) etching microwells on a silicon wafer as an initial mold;

(2) pouring polydimethylsiloxane over the initial mold and removing the polydimethylsiloxane after molding to produce a second mold with microwells; and (3) pouring molten agarose with a mass to volume ratio of 4% to 6% on the second mold, cooling and molding followed by removing the agarose to obtain the microwell plate.

8. An ultra-high-throughput single cell sequencing method comprising the following steps:

(1) preparing following reagents:

a) molecular labeled microbeads, the molecular labeled microbead comprising a microbead body and a coupled molecular label sequence, the molecular label sequence comprising in sequence:

a universal primer sequence, serving as a primer binding region during PCR amplification;

a first cell barcode sequence; and a first bridge sequence;

b) a specific molecular barcode transposase-embedded complex, comprising Tn5 transposase and a specific molecular barcode sequence, wherein the specific molecular barcode sequence comprises in sequence:

a second bridge sequence;

a second cell barcode sequence, forming a cell barcode sequence in conjunction with the first cell barcode sequence, the cell barcode sequence being used for identifying a cell from which each sequence in the constructed sequencing library is derived; and a Mosaic Ends sequence for binding to the Tn5 transposase, the Mosaic Ends sequence having a double-stranded structure, wherein one strand is ligated with the second cell barcode sequence; and c) a bridge primer for ligating the above-mentioned label sequence in a) and the specific molecular barcode sequence in b), the bridge primer having, on both ends, a sequence complementary to the first bridge sequence and the second bridge sequence, respectively;

(2) extracting nuclei from a cell sample to be sequenced;

(3) adding the specific molecular barcode transposase-embedded complex to the extracted nuclei of step (2) for transposition reaction;

(4) compartmentalizing one or more of the transposed nuclei with one molecular labeled microbead by microwell-plate technology or microfluidic technology, and lysing the nuclei under the action of a lysis buffer, incubating, and then ligating the first bridge sequence with the second bridge sequence by the pairing of bridge primers with the first bridge sequence and the second bridge sequence, respectively, followed by ligation through a ligase, such that a molecular label sequence-specific molecular barcode sequence-transposase-accessible chromatin genome sequence coupled to the microbead is obtained;

(5) collecting the microbeads coupled with the molecular label sequence-specific molecular barcode sequence-transposase-accessible chromatin genome sequence, and performing PCR amplification to obtain a transposase-accessible chromatin genome sequence having the first cell barcode sequence, the second cell barcode sequence and the specific molecular barcode sequence; and (6) constructing a chromatin accessibility sequencing library with product obtained from step (5), and then performing high-throughput sequencing to obtain information of specific genome accessibility of millions of single cells;

wherein, the preparation method of the molecular labeled microbeads comprises the following steps:

classifying the bridge primers for synthesizing the molecular label sequences into a plurality of primers in accordance with a number of specific fragments, each primer comprising a specific fragment, there being adapter sequences between each of the primers for bridging, ligation and complementing each other, wherein a primer corresponding to a 5' end of the molecular label sequence further comprises the universal primer sequence, and a primer corresponding to a 3' end of the molecular label sequence further comprises the first bridge sequence; and coupling the primer corresponding to the 5' end of the molecular label sequence to the microbead body, then annealing and extending remaining primers in sequence by PCR, and cascading remaining specific fragments of the molecular label sequence in sequence from the 5' end to the 3' end to prepare and obtain the molecular labeled microbead; and wherein, the molecular label sequence is: 5'-TTTAGGGATAACAGGGTAATAAGCAGTGGTATCAACGCAGAGTACGTNNNNNN CGACTCACTACAGGGNNNNNNTCGGTGACACGAT CGNNNNNNTCGTCGGCAG CGTC-3' (SEQ ID No. 4), wherein, N represents any one of A/T/C/G and is randomly synthesized.

9. The ultra-high-throughput single cell sequencing method according to claim 8, wherein, the microbead is coupled to the molecular label sequence in such a way comprising: replacing a hydroxyl group with an amine group at C6 position of a nucleotide at the 5' end of the molecular label sequence, having the surface of the microbead modified with a carboxyl group, and coupling through condensation of an amino group and the carboxyl group.

10. The ultra-high-throughput single cell sequencing method according to claim 8, wherein, the first cell barcode sequence comprises a plurality of specific fragments, and the second cell barcode sequence comprises at least one specific fragment, the specific fragments at different locations being selected from the same or different libraries of specific fragments, and the first cell barcode sequence and the second cell barcode sequence identifying cells by using different combinations and arrangements of the specific fragments.

11. The ultra-high-throughput single cell sequencing method according to claim 8, wherein, the cell sample to be sequenced comprises 2 or more types of cells.

12. The ultra-high-throughput single cell sequencing method according to claim 8, wherein, the microbead body is a magnetic microbead;

the intracellularly reverse transcribed cells or transposed nuclei are added to a microwell plate, followed by the addition of the molecular labeled microbead, the microwell in the microwell plate having a diameter big enough to just accommodate one molecular labeled microbead and one or more cells or nuclei; and the capture rate of cells or nuclei in the microwell plate is maintained at over 80%; and the capture rate of the molecular labeled microbead in the microwell plate is over 99%.

* * * * *

SEQUENCE LISTING

```
<160> NUMBER OF SEQ ID NOS: 14

<210> SEQ ID NO 1
<211> LENGTH: 68
<212> TYPE: DNA
<213> ORGANISM: Artificial Sequence
<220> FEATURE:
<223> OTHER INFORMATION: Synthesized
<220> FEATURE:
<221> NAME/KEY: misc_feature
<222> LOCATION: (48)..(53)
<223> OTHER INFORMATION: n is a, c, g, t or u.

<400> SEQUENCE: 1

tttagggata acagggtaat aagcagtggt atcaacgcag agtacgtnnn nnncgactca     60

ctacaggg                                                              68


<210> SEQ ID NO 2
<211> LENGTH: 36
<212> TYPE: DNA
```

-continued

<213> ORGANISM: Artificial Sequence
<220> FEATURE:
<223> OTHER INFORMATION: Synthesized
<220> FEATURE:
<221> NAME/KEY: misc_feature
<222> LOCATION: (16)..(21)
<223> OTHER INFORMATION: n is a, c, g, t or u.

<400> SEQUENCE: 2
cgatcgtgtc accgannnnn nccctgtagt gagtcg 36

<210> SEQ ID NO 3
<211> LENGTH: 35
<212> TYPE: DNA
<213> ORGANISM: Artificial Sequence
<220> FEATURE:
<223> OTHER INFORMATION: Synthesized
<220> FEATURE:
<221> NAME/KEY: misc_feature
<222> LOCATION: (15)..(20)
<223> OTHER INFORMATION: n is a, c, g, t or u.

<400> SEQUENCE: 3
gacgctgccg acgannnnnn cgatcgtgtc accga 35

<210> SEQ ID NO 4
<211> LENGTH: 109
<212> TYPE: DNA
<213> ORGANISM: Artificial Sequence
<220> FEATURE:
<223> OTHER INFORMATION: Synthesized
<220> FEATURE:
<221> NAME/KEY: misc_feature
<222> LOCATION: (48)..(53)
<223> OTHER INFORMATION: n is a, c, g, t or u.
<220> FEATURE:
<221> NAME/KEY: misc_feature
<222> LOCATION: (69)..(74)
<223> OTHER INFORMATION: n is a, c, g, t or u.
<220> FEATURE:
<221> NAME/KEY: misc_feature
<222> LOCATION: (90)..(95)
<223> OTHER INFORMATION: n is a, c, g, t or u.

<400> SEQUENCE: 4
tttagggata acagggtaat aagcagtggt atcaacgcag agtacgtnnn nnncgactca 60
ctacagggnn nnnntcggtg acacgatcgn nnnnntcgtc ggcagcgtc 109

<210> SEQ ID NO 5
<211> LENGTH: 36
<212> TYPE: DNA
<213> ORGANISM: Artificial Sequence
<220> FEATURE:
<223> OTHER INFORMATION: Synthesized

<400> SEQUENCE: 5
cgtcgtgtag ggaaagagtg tgacgctgcc gacgac 36

<210> SEQ ID NO 6
<211> LENGTH: 64
<212> TYPE: DNA
<213> ORGANISM: Artificial Sequence
<220> FEATURE:
<223> OTHER INFORMATION: Synthesized
<220> FEATURE:
<221> NAME/KEY: misc_feature
<222> LOCATION: (22)..(37)
<223> OTHER INFORMATION: n is a, c, g, t or u.
<220> FEATURE:
<221> NAME/KEY: misc_feature -continued
<222> LOCATION: (63)..(63)
<223> OTHER INFORMATION: v is a, c or g.
<220> FEATURE:
<221> NAME/KEY: misc_feature
<222> LOCATION: (64)..(64)
<223> OTHER INFORMATION: n is a, c, g, t or u.

<400> SEQUENCE: 6
acactctttc cctacacgac gnnnnnnnnn nnnnnnnttt tttttttttt tttttttttt 60 ttvn 64

<210> SEQ ID NO 7
<211> LENGTH: 34
<212> TYPE: DNA
<213> ORGANISM: Artificial Sequence
<220> FEATURE:
<223> OTHER INFORMATION: Synthesized
<220> FEATURE:
<221> NAME/KEY: misc_feature
<222> LOCATION: (26)..(33)
<223> OTHER INFORMATION: n is a, c, g, t or u.

<400> SEQUENCE: 7
aagcagtggt atcaacgcag agtgannngg nnnb 34

<210> SEQ ID NO 8
<211> LENGTH: 23
<212> TYPE: DNA
<213> ORGANISM: Artificial Sequence
<220> FEATURE:
<223> OTHER INFORMATION: Synthesized

<400> SEQUENCE: 8
aagcagtggt atcaacgcag agt 23

<210> SEQ ID NO 9
<211> LENGTH: 35
<212> TYPE: DNA
<213> ORGANISM: Artificial Sequence
<220> FEATURE:
<223> OTHER INFORMATION: Synthesized

<400> SEQUENCE: 9
cgtcgtgtag ggaaagagtg tgacgctgcc gacga 35

<210> SEQ ID NO 10
<211> LENGTH: 34
<212> TYPE: DNA
<213> ORGANISM: Artificial Sequence
<220> FEATURE:
<223> OTHER INFORMATION: Synthesized

<400> SEQUENCE: 10
gtctcgtggg ctcggagatg tgtataagag acag 34

<210> SEQ ID NO 11
<211> LENGTH: 50
<212> TYPE: DNA
<213> ORGANISM: Artificial Sequence
<220> FEATURE:
<223> OTHER INFORMATION: Synthesized
<220> FEATURE:
<221> NAME/KEY: misc_feature
<222> LOCATION: (22)..(31)
<223> OTHER INFORMATION: n is a, t, c or g.

<400> SEQUENCE: 11

-continued

```
acactctttc cctacacgac gnnnnnnnnn nagatgtgta taagagacag              50


<210> SEQ ID NO 12
<211> LENGTH: 19
<212> TYPE: DNA
<213> ORGANISM: Artificial Sequence
<220> FEATURE:
<223> OTHER INFORMATION: Synthesized

<400> SEQUENCE: 12

ctgtctctta tacacatct                                                 19


<210> SEQ ID NO 13
<211> LENGTH: 63
<212> TYPE: DNA
<213> ORGANISM: Artificial Sequence
<220> FEATURE:
<223> OTHER INFORMATION: Synthesized

<400> SEQUENCE: 13

gaacgacatg gctacgatcc gacttgcctg tccgcggaag cagtggtatc aacgcagagt   60

acg                                                                  63


<210> SEQ ID NO 14
<211> LENGTH: 50
<212> TYPE: DNA
<213> ORGANISM: Artificial Sequence
<220> FEATURE:
<223> OTHER INFORMATION: Synthesized
<220> FEATURE:
<221> NAME/KEY: misc_feature
<222> LOCATION: (26)..(35)
<223> OTHER INFORMATION: n is a, t, c or g.

<400> SEQUENCE: 14

tgtgagccaa ggagttgttg tcttcnnnnn nnnnngtctc gtgggctcgg              50
```